(12) United States Patent
Horton et al.

(10) Patent No.: US 8,174,691 B1
(45) Date of Patent: May 8, 2012

(54) DETECTION OF A COMPONENT OF INTEREST WITH AN ULTRAVIOLET LASER AND METHOD OF USING THE SAME

(75) Inventors: Matthew Horton, Jonesboro, AR (US); Robyn Hannigan, Jonesboro, AR (US)

(73) Assignee: Arkansas State University—Jonesboro, State University, AR (US)

( * ) Notice: Subject to any disclaimer, the term of this patent is extended or adjusted under 35 U.S.C. 154(b) by 1029 days.

(21) Appl. No.: 12/048,310

(22) Filed: Mar. 14, 2008

Related U.S. Application Data

(60) Provisional application No. 60/918,111, filed on Mar. 15, 2007.

(51) Int. Cl.
*G01N 1/10* (2006.01)
(52) U.S. Cl. ......... 356/246; 356/244; 356/326; 356/301
(58) Field of Classification Search .................. 356/246, 356/244, 326, 301
See application file for complete search history.

(56) References Cited

U.S. PATENT DOCUMENTS

| | | | | |
|---|---|---|---|---|
| 4,784,486 | A * | 11/1988 | Van Wagenen et al. | 356/301 |
| 6,100,975 | A * | 8/2000 | Smith et al. | 356/301 |
| 7,027,147 | B2 * | 4/2006 | Steenhoek et al. | 356/246 |
| 7,221,861 | B1 | 5/2007 | Hannigan | |
| 7,336,860 | B2 * | 2/2008 | Cyr et al. | 385/12 |

OTHER PUBLICATIONS

Alexander et al. (1993) "Laser Desoprtion in a Quadrapofe Ion Trap: Mixture Analysis Using Positive and Negative Ions" Analytical Chemistry 65:1609.

Weickhardt and Tonnies (2003) "Rapid analysis of complex mixtures by means of resonant laser ionization mass spectrometer" Laser in Environmental and Life Sciences, Hering, P., Lay JP, Stry, S (eds), Springer Verlag. New York, 193-221.
Vorm et al. (1994) "Improved Resolution and Very High Sensitivity in MALDI TOF of Matrix Surfaces made by Fast Evaporation" Analytical Chemistry, 66:3281-3287.
Yinon, J. (2002) "Field detection and monitoring of explosives" Trends in Analytical chemistry, 21(4):292-301.
Committee on the Review of Existing and Potential Standoff Explosives Detection Techniques, National Research Council (2004), Existing and Potential Standoff Explosives Detection Techniques, National Academies Press, Washington D.C.
Harper et al. (2005) Identification of dominant odor chemicals emanating explosives for use in developing optimal training aid combinations and mimics for canine detection 67(2):313-327.
Lopez-Moreno et al. (2006) "Test of a stand-off laser-induced breakdown spectroscopy sensor for the detection of explosive residues on solid surfaces" Journal of Analytical Atomic spectrometry, 21:55-60.
Halasz et al. (2002) "Detection of explosives and their degradation products in soil environments" Journal of Chromatography A 963:411-418.
Lebedev et al. (2005) "Mass spectrometry in identification of ecotoxicants including chemical and biological warfare agents" Toxicology and Applied Pharmacology 207:S451-S458.

(Continued)

*Primary Examiner* — Layla Lauchman
(74) *Attorney, Agent, or Firm* — Joe D. Calhoun; Rashauna A. Norment

(57) ABSTRACT

A device is provided for detection and analysis of a component of interest in a sample comprising a small sample cell used with an ultra violet laser. The energy of the laser is spread over an area such that energy density is above desorption threshold, but the sample not ablated. The device provides for rapid and reliable detection of a component of interest, and a method of using the same. The sample cell provides decreased dispersion of the sample.

15 Claims, 23 Drawing Sheets

OTHER PUBLICATIONS

Yan (2002) "Sulfur and nitrogen chemiluminescence detection in gas chromatographic analysis" Journal of Chromatograph A. 976:3-10.

Nyarady et al. (1985) "Redox Chemiluminescence Detector: Application to Gas Chromatography" Analytical Chemistry 57:2074-2079.

Yan (1999) "Detection by ozone-induced chemiluminescence in chromatography" Journal of Chromatography A. 842:267-308.

Pinnaduwage et al. (2003) "Explosives: a microsensor for trinitrotoluene vapour" Nature 425:474.

Morgan et al. (1999) "Improved detection of explosive residues by laser thermal desorption" Johns Hopkins APL Technical Digest 20(3):389-395.

Weickhardt and Tonnies (2003) "Rapid analysis of complex mixtures by means of resonant laser ionization mass spectrometer" Laser in Environmental and Life Sciences, Hering, P., Lay JP, Stry, S (eds), Springer Verlag, New York, 193-221.

Elobeid et al. (2005) "Speciation analysis with GC-ICP-MS: organometal detection in tobacco smoke" G. Holland and D. Bandura (eds) Plasma Source Mass Spectrometry: Current Trends and Future Developments. Royal Society of Chemistry, London, UK 80-88.

Horton, M. Rougeu, B. and Hannigan, R. (Mar. 16, 2006) "Laser Ablation GC-MS: New Instrument Interface for In Situ Analysis of volatile Organic Compounds" SETAC Conference.

\* cited by examiner

DETECTION OF A COMPONENT OF INTEREST WITH AN ULTRAVIOLET LASER AND METHOD OF USING THE SAME

REFERENCE TO RELATED APPLICATION

This application claims priority to previously filed and provisional application U.S. Ser. No. 60/918,111, filed Mar. 15, 2007, the contents of which are incorporated herein by reference.

GOVERNMENT FUNDING

Work described herein was funded, at least in part, by the federal government, Department of Defense, Ref No. W911M-06-C-0001, and the United States government has certain rights in the invention.

BACKGROUND

The need to analyze compounds in a composition exists in a myriad of applications. A variety of means and methods have developed to obtain an intact sample, separate the different components and analyze the separated components. Detection and characterization of components of a sample is relevant, for example, where determining the constituents of biological samples, solid samples, and organic samples. However, improvements in existing systems are needed in the manner in which the sample is collected, and in particular in collecting and extracting components of interest a sample from a solid substance.

For example, in a number of industrial and research settings, studies of organic matter in solid samples involve analysis of compounds such as bitumen, kerogen, organic carbon, hydrocarbons, and fatty acids. Current methods of analysis of organic matter and hydrocarbons include, by way of example, a series of organic extractions of total organic matter and extractable organic matter followed by further extractions necessary to isolate potential compounds of interest such as hydrocarbons, normal, branched and cyclic alkanes, other hydrocarbons (n-alkanes, steranes and hopanes) and fatty acids.

In other arenas, the detection of particular components that would alert to the presence of a dangerous substance includes analysis of the components of explosives, harmful biologicals and chemical agents and the presence of fissionable isotopes. Each such application requires a system that can extract the component of interest, contain it in a manner optimizing analysis, and detection of the component of interest, preferably quickly and without exposure to the dangerous components or compounds.

Small scale explosives such as TNT (2,4,6-Trinitrotoluene), DNT (2,6-Dinitrotoluene and 2,4-Dinitrotoluene and 3,4-Dinitrotoluene), PETN (Pentaerythritol tetranitrate), and RDX (1,3,5-Trinitro-1,3,5,7-triazacyclohexane) are examples of the type of compounds for which there is a need to develop a fast system to detect the compounds or their constituents, for use, for example, by law enforcement and military personnel, as well as those involved in environmental clean-up activity.

Detection of weapons of mass destruction is another example of one such application. Biological weapons, by way of example, include anthrax, smallpox, plague, botulism, and Tularemia among various bacterial, viral and other biologicals. One means to detect such biologicals uses the polymerase chain reaction, typically used with a PCR thermal cycler or machine, and is available as real-time PCR. Olson (2004). It provides rapid nucleic acid amplification with continuous monitoring of accumulated products during cycling. Other examples include another type of PCR, found by Bell et al. (2003), the LightCycler PCR, that was very efficient at identifying anthrax strains isolated by culture, successfully identifying all 31 strains of B. anthracis tested. Bell (2003). Other methods are Serology and Histopathology. CDC (2005). One example is the BASIS (Biological Aerosol Sentry and Information System) system designed by the government laboratories at Los Alamos, in conjunction with Lawrence Livermore National Laboratories and Rupprecht and Patashnick Co. (a New York manufacturer of air samplers) which has been placed at many urban areas, sports arenas, airline terminals, bridges and tunnels, government offices, shopping plazas, and busy street corners. This technology uses a series of filters to capture bacteria, viruses, and tiny particles followed by PCR and more sophisticated assays to identify the strain and investigate whether the organism has been genetically modified to make it more virulent or resistant to drugs. The BASIS system has a very high sensitivity and a rate of false positives of less than one in every 20,000 assays. The result of the system is that it can detect and alert the presence of an aerosolized bio-weapon in about eight hours from the time of detection which gives those infected a better chance of seeking medical attention in time to prevent death or serious illness. (LoPresti (2006).

Chemical weapons and improvised explosive devices (IED's) are another example of substances in which detection of the presence of the compounds or constituents in a rapid and efficient manner is desired. Examples of modern chemical warfare agents include VX, Tabun, Sarin, Soman, Ricin, Phosgene, and Mustard gas which can be produced as liquids, solids, or vapors. Some liquid agents are volatile and convert to vapor form quickly while others are nonvolatile and emit little vapor at room temperatures and persist in the environment. Solid agents can sometimes be aerosolized as an inhalable powder and liquid agents can be sprayed as aerosols or fixed on a solid matrix. NRC (2004)-1.

Because chemical substances typically have distinctive and measurable mass, chemical, and electromagnetic properties, many existing physical mechanisms (other than detection by affected humans) listed by the Department of Homeland Security, U.S. Navy, and the U.S. Army as in use or in development could be employed for detection, identification, and classification of signatures derived from the presence or use of chemical weapons. NRC (2001)-1 and NRC (2004)-1. Perhaps most importantly among these detection capabilities are standoff detection devices. Standoff detection puts individuals and vital assets a safe physical distance from the chemical source. A few examples of existing standoff technologies are the (CWDD) AN/KAS-1, RSCAAL, JSLSCAD, and LIDAR.

The Chemical Weapon Directional Detector (CWDD) AN/KAS-1 is a multispectral passive infrared (IR) imaging system that uses spectral filters to detect IR radiation emitted by nerve agents and can be remotely operated with the capability to send the sensor's video images to various locations. The M-21 RSCAAL (remote sensing chemical agent alarm) is an automatic, scanning, passive, multispectral infrared sensor that is similar to the AN/KAS-1. It is designed to detect chemical agent vapor clouds due to changes in IR energy in remote objects due to the use or presence of chemical agents. The JSLSCAD (joint service lightweight standoff chemical agent detector) system is very similar to the RSCAAL except that it is a hyperspectral system based on Fourier transform infrared spectroscopy (FT-IR). LIDAR technology employed by the U.S. Army Artemis program uses a laser to transmit radio waves and an optical telescope to receive them. The Artemis program using LIDAR technology is a real time, standoff detection system that monitors chemical agent contamination for recognition, avoidance, and decontamination. NRC (2004)-1; Abrams (2000).

Other technologies are Ion Mobility spectroscopy, Gas Chromatography, Photo acoustic IR spectroscopy, Surface acoustic wave, and Photo ionization. These technologies are considered ready to near-term instruments capable of chemical agent detection with low detection limits (ppm, ppb).

Detection of nuclear weapons and activity are derived from the fissionable isotopes $^{235}U$, $^{239}Pu$, and $^{233}U$. The signatures from spontaneous decay of plutonium weapons are gamma rays and neutrons. The spontaneous neutron fission output can be detected through the use of detectors able to detect excess thermal neutrons at levels above background flux. Gamma ray output would also have to be detected above the background flux levels. While $^{235}U$ is more difficult to detect due to a low spontaneous fission rate, the characteristic low gamma ray emission spectrum can be used to detect and identify these weapons. Due to the natural gamma ray background and low gamma ray energy emissions of $^{235}U$ however, detection ranges can be difficult. NRC (2001)-2. Gamma ray detection technologies would also apply to radiological weapons since the main source of these weapons is gamma ray emitters. Some of the detection technologies listed by the Army for radiological and nuclear weapons detection that are either ready or in research and development are passive gamma ray detection devices employing germanium crystals, sodium iodide crystals, and mercuric iodide, as well as passive neutron detection systems which employ silicon strips, scintillating glass fibers, and pulsed neutron and radioactive gamma sources. These technologies (as well as the many other applicable technologies) all have potential, through implementation, of adding measures of civilian and military safety.

Many examples of new technologies, as well as new ways to implement old or existing technologies are present for detection of TED's in the home front and the battle theatre. In general, current field deployable explosive detection instruments are designed to exploit the chemical properties of explosives by three methods: vapor and particle detection, radiation detection, and biochemical detection. Yinon (2002). Many of these technologies involve both spectroscopic and spectrometric approaches. As the name implies, spectroscopy techniques involve specific interactions of the explosive material with some source of electromagnetic radiation for detection and generally reveals structural and functional group information. The spectrometric techniques involve physical detection of ions derived from the atoms and molecules comprising the explosive threat.

According to a recent report on potential standoff technologies for the detection of explosives by the National Academies of Science, optical techniques for trace detection in either the vapor, particulate phase, or both include transmission and reflection spectroscopy in the infrared, UV-Vis, and microwave regions, photoacoustic spectroscopy, cavity ringdown spectroscopy (CRDS), light detection and amplification (LIDAR), differential absorption LIDAR (DIAL), and differential reflection LIDAR (DIRL). NRC (2004)-2. Non-linear optical techniques, which offer potential improvements in signal to noise values and optimize their luminescence (Harper (2005)) include coherent anti-Stokes Raman scattering (CARS), optical phase conjugation, and coherent control.

Electromagnetic imaging systems for bulk detection include infrared, terahertz, microwave, and radar. X-ray, neutron, electromagnetic, and gamma ray technologies are also know to have potential for bulk detection. Of these techniques, microwave and terahertz have potential as standoff technologies for detecting concealed explosives; however these techniques have the downside of lacking chemical specificity. NRC (2004)-2.

Lasers are also beginning to have a prominent role for desorption, ionization, or detonation of explosives. Examples are LIDAR, CRDS, spontaneous Raman instruments, laser induced breakdown spectroscopy (LIBS), laser ionization time of flight mass spectrometry (TOF-MS), laser desorption mass spectrometry (LD-MS), and a new army technology called the Zeus system for detonation of LED's. The LIDAR technology has shown promise for standoff potential however, they suffer from an assortment of electronic spectral features for large molecules. NRC (2004)-2.

A newer LIDAR type technology that uses linear or spontaneous Raman has been developed that boasts standoff detection of high explosives at 50 meters. Carter (2005). A Nd:YAG laser (532 nm) is used as the excitation source while light is collected with a telescope coupled to a spectrograph with a intensified charge coupled device (ICCD) as the detector. The downside to the standoff claim is that although the explosive samples analyzed only contained 4 to 8% TNT, RDX, or PETN, the samples were placed into a test-tube in plain sight and the laser was aimed directly on to it. In addition, the 50 meters standoff capability claimed was actually based on the placement of a mirror 27 meters away that was used to reflect the laser and telescope field of view onto a sample approximately 50 meters away. In this way, over 70% of the signal was lost. Nevertheless, the method was found to be adequate at a distance of 27 meters although its potential for locating explosive devices with no prior knowledge of its coordinates is limited.

The LIBS technique has also shown some promise for standoff applications, Lopez-Moreno (2006), however a drawback to the technique is that it primarily uses N and O atomic emission lines for identification and these signals have spectral contributions from ambient air making quantification difficult. In addition, although a spectral fingerprint can be established for each explosive with this technique, peak ratios and molecular band analysis are used for identification which can lead to long data analysis times, especially since this technique is fairly new and extensive fingerprint libraries have not been established. This bottleneck is somewhat remedied with the fact that the N and O abundances in explosives are relatively unique. Yinon (2002). Nevertheless, explosives placed on aluminum foil were detected at distances of 45 meters, proving that this technique has some standoff utility and may merit further development in the future. Lopez-Moreno (2006).

Two of the main techniques for trace explosive detection are Gas Chromatography Mass Spectrometry (GC-MS) and an Ion Mobility Spectrometry (IMS). The GC-MS is known as the "gold standard" for chemical analysis (Grob (2004)) and according to Harper et al. (2005), IMS instruments are the most commonly used explosive screening devices deployed in airports due to their ability to detect explosive particles collected on sample swipes. Harper (2005). A common sampling device for GC introduction which aids in the sampling of explosive traces is the solid phase microextraction (SPME) device which uses a special polymer to trap compounds of interest for subsequent GC desorption and separation. Harper, supra, and Halasz (2002).

The theory of gas chromatography has been described elsewhere (Grob (2004)) but one important aspect is that it can be performed rapidly in a technique generally known as "fast GC" which involves large bore columns combined with high flow rates which is important for quickly identifying terrorist threats. Another beneficial aspect of GC is the availability of capillary columns with specialized stationary phases such as the Restek TNT and TNT2 columns. The SPME device can also be used with GC by desorbing analytes collected on the specialized polymer directly in the injector port on the GC. Beginning with a general method such as EPA method 8095 for explosive analysis, many parameters can be altered such as injector temperature, oven programs, column lengths, and flow rates to provide for compound specific optimized separation and resolution. A useful feature of the GC is that it can be interfaced to a variety of detectors such as MS, Electron Capture Detector (ECD), Flame Ionization Detector (FID), NCD, IMS, and many others.

A mass spectrometer consists of an ionization source such as electron or chemical ionization, a mass analyzer such as a quadrapole or ion trap, and a detector such as an electron or photomultiplier. Mass spectrometry allows for very selective detection due to the production of characteristic fragmentation breakdown patterns of molecules. Depending on the ionization source the molecular ion is often apparent which is useful for MW determination. MS is also a very sensitive detector which has been shown to detect femtogram and attogram quantities of analytes. Lebedev (2005). Identification of molecules is made easier with the libraries of fragmentation patterns used for identification such as the NIST (National Institute of Standards; see for example www.nist.gov) spectral library which makes the MS a very reliable detector. Mass spectrometry has been shown to have utility for fast detection of chemicals and biological warfare adding to its utility as a versatile detector. Lebedev, supra.

Several portable GC-MS instruments are available for mobile and in situ detection of explosives. Agilent has a GC-MS (Agilent 6890N/5973GC/MSD) included as a part of two of their mobile laboratories. One is the modular/flyaway laboratory which is durable enough to be packaged in boxes and dropped into the incident site from an airplane for rapid response to chemical and biological agents. The other is the Agilent Mobile Lab which is a laboratory inside an RV style truck. A few other portable GC-MS instruments are the HAP-SITE available from Inficon, Inc., the CT-1128 from Constellation Technology, and the MM2 from Brunker Daltonics, all of which have found use for field analysis of chemical and biological agents.

IMS can be interfaced to a GC but is often used as a stand-alone instrument. The IMS uses an electron source to create negative ions at ambient pressures along with temperatures around 100° C. The ions are then gated with a charged electrode into a drift tube and accelerated towards the detector with a strong electric field of about 15 kilovolts per meter. The ions are then separated based on their drift time or "mobility". The drift time of the ions is characteristic of their size/charge ratio and cross-sectional area and they arrive at the detector in order from fastest to slowest which generates a signal response that is characteristic of the chemical composition of the analyte. The IMS is not as selective as GC-MS but because of its small size, fast response, relatively low cost and simple instrumentation to maintain and operate, it has been widely deployed for field detection of explosives, biological materials, chemical weapons, and drugs. NRC (2004)-2.

An example of a new technology using both GC and IMS is the EGIS Defender trace explosive detection system from Thermo Electron Corporation now being used in airports to analyze swipes taken of passports, laptop cases, people, etc. The system uses a fast GC front end for quick separation of explosives from other sample analytes, followed by a micro differential IMS for detection. The system can detect the presence of an explosive in 15 seconds with a rate of false positives lower than 3%. Although samples have to be physically collected, which makes the instruments standoff potential nonexistent, the 15 second analysis time is very attractive for immediate responses to explosive threats.

There exists a need to develop improved methods of detecting components of a compounds by a system with faster, more sophisticated, rugged, sensitive, and selective detection technologies for reliable field portable devices in harsh environments with the ability to discriminate between explosive threats and normal background contamination, and useful in analyzing organic matter in solid samples. The ideal detector would also have a low rate of false positives, employ orthogonal detection, and, when detecting a dangerous compound, be standoff. However, these devices must be simple to operate with little or no technical expertise for operation required.

All references cited are incorporated herein by reference.

SUMMARY OF THE INVENTION

The invention provides a means and method for rapid detection of a component of a compound which in an embodiment employs a small sample cell. The small cell sample container in a preferred embodiment is one of about 0.1 $cm^3$ to about 8 $cm^3$, in another embodiment it is about 1 to about 5 $cm^3$, and in yet another embodiment is about 5 $cm^3$. Another embodiment provides using a UV laser where the energy density is above the desorption threshold, but does not ablate the sample. In a further embedment the laser is combined with a gas chromatograph and also with a nitrogen chemiluminescence dector, mass spectrometer or both. Improved interface connections in the device are also provided, which removes the need for a stationary phase and provides for movement of the sample through the device with reduced loss of sample material.

DETAILED DESCRIPTION OF PREFERRED EMBODIMENTS OF THE INVENTION

Figure 1:
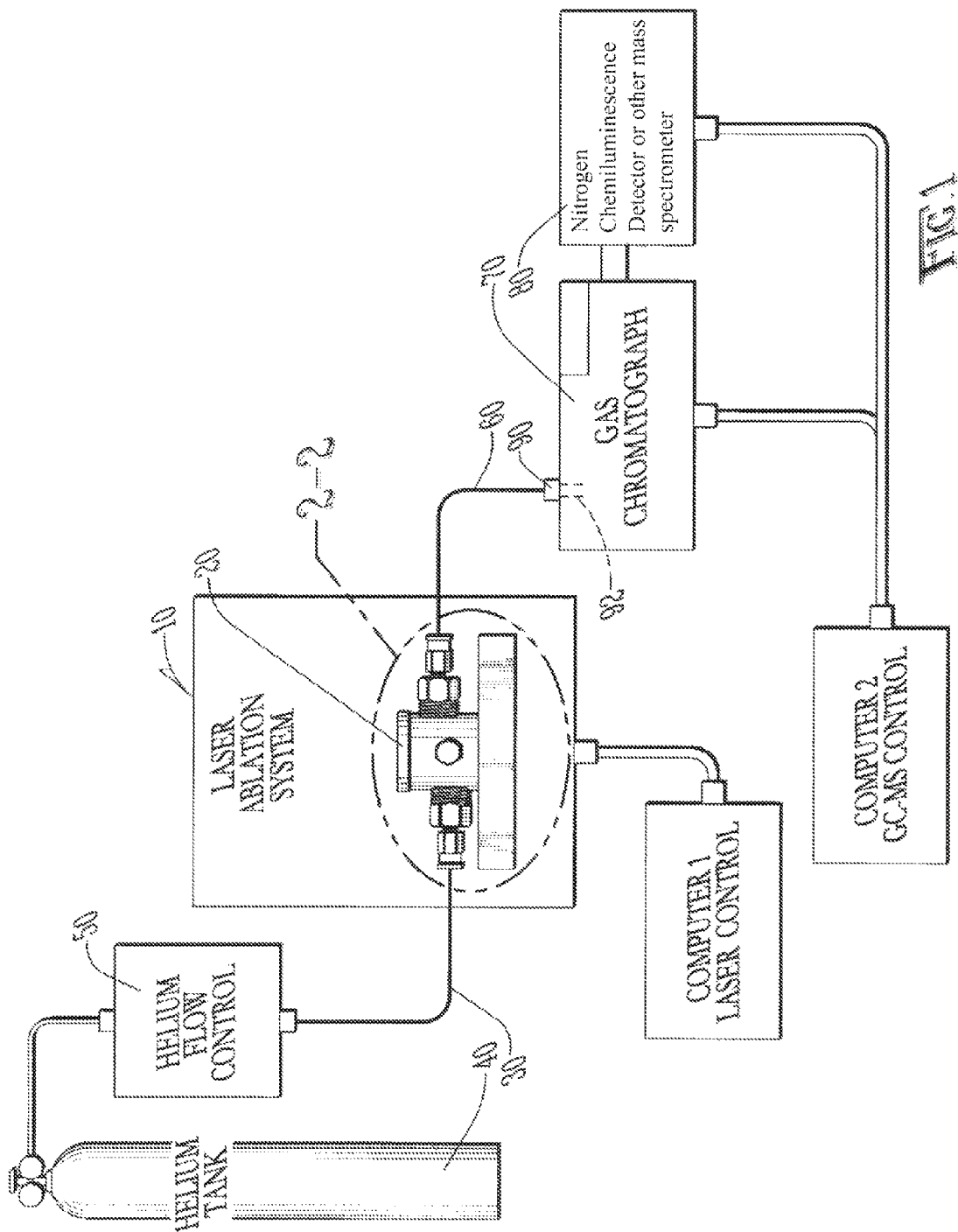
FIG. 1 shows a schematic of an embodiment of a device of the invention.

The invention is to an improved means and method of analyzing chemicals. The invention is useful in analyzing a wide range of compounds. The compounds discussed above are among those that can be analyzed using the invention, including without limitation and by way of example organic compounds, biologicals, compounds and constituents of explosive devices and substances used to make same. A discussed below, the invention provides the ability to analyze a solid substance having the compounds of interest or component thereof. Any compound which can be removed from its solid substrate using a laser as described here can be detected using the invention.

Sample cells used in laser ablation instruments and the like currently use large sample cells to introduce the sample into the instrument for measurement. Typically such sample cells are in the range of 250 centimeters $(cm)^3$. While these large sample cells are ideal for sample delivery to elemental analyzers such as ICP-MS, they are too large for sufficient gas chromatograph analysis due to sample drift and dispersion, and can complicate mass spectrometer vacuum requirements. The spreading of the sample prevents accurate measurements by GC-MS. Instead, the sample cell here is considerably smaller, in the range of about 0.1 $cm^3$ to about 7 or 8 $cm^3$. The sample cell could be even smaller than 0.1 $cm^3$, but ideally volumes of at least about 1 to 5 $cm^3$ are more practical. In a preferred embodiment, the sample cell is about 5 $cm^3$. As a result, reliable accurate measurements of the sample introduced into the instrument are possible and use of a gas chromatograph is an option. This allows for use of the application in a wide range of applications. The newly developed smaller laser ablation sample cell is unique in that it allows for small volume sample sizes to be delivered into gas chromatography instruments, which are ideal for molecular analysis. Because the cell is specifically designed for sampling of solid materials by laser ablation, organic molecular analyses can be conducted on a suite of solid matrices. Some specific applications for LA-GC-MS (laser ablation, gas chromatography-mass spectrometry) analysis using the cell, though certainly not all, are black shale, rice endosperm bran, fish otolith, explosives trapped in a swipe matrix, coal, tobacco roots, tissues (brain, liver, kidney, intestine), and several petroleum products. So long as any solid sample absorbs ultraviolet laser radiation (for example, using wavelengths 266 and 213) to the point that the molecule of interest will vacate its substrate, the sample cell is an appropriate means for conducting LA-GC-MS analyses.

Further, the invention is directed to using a laser ablation system not to ablate the sample, but to excite it to the point the component of interest is removed from the solid substrate and can be moved through the system to the instrument of analysis. Unlike prior systems, this does not ablate the substances, which creates a dry nanoparticle stream, but provides for direct samples of solids and volatilization of the materials of the components of interest. By varying specific parameters such as energy level, pulse frequency, bursts, and spot size, the UV laser was proven to be adequate for sample introduction when a low volume sample cell was employed. Selective and sensitive detection of components of interest was achieved. The wavelength of such laser is typically 213 to 266, and in a preferred embodiment is 266. The laser is adjusted so that instead of ablating the sample, it causes the component of interest to vacate the substrate. A UV laser is adjusted so that the energy of the laser is spread over an area and the energy density is above desorption threshold, but does not ablate. In an embodiment the energy fluence of the laser is about 2.0 to about 3.0 $J/cm^3$. Fluence is a measurement of energy per area. Used here, fluence indicates the amount of total energy spread out over an aperture imaged area. For example, in one version, a hole in a wheel is placed in the beam path to change diameter once it is refocused by the objective just before hitting the sample. The spot is imaged onto the sample so that a crater of particular size can be ablated in it. As set out in one example below, beginning with a 200 µm aperture the z-stage is defocused 1 mm to increase sample area (to about 500 µm) and decreases effective energy density such that measure fluence (measured in J(energy)/$cm^2$) is just high enough to desorb molecules of interest while avoiding any visible ablation of the substrate.

A variety of variations in the particular steps used are available to one skilled in the art, and the same objective of spreading energy of the laser over an area to achieve the desorption threshold but not ablate. In one embodiment of the invention, the energy range of the laser is reduced by at least about 20% or more, in another embodiment reduced by at least about 50% or more and in another to about 70% or more. In one example below, the energy was adjusted to about 0.7 to 1.0 mJ. In the example, pulse frequency less than about 20 Hz. Further embodiments provide the laser spot size is about 10 to 100 µm, and in another is about 200 µm. The number of pulses was less than about 50 shots, and in a preferred embodiment was about 10 shots. In a preferred embodiment, the device incorporates either a Nitrogen Chemiluminescence Detector (NCD) or Mass Spectrometer (MS) or both. Selectivity of the MS was enhanced by using the Selective Ion Mode (SIM).

Thus, samples of solids, rapid detection and avoidance of time and expense in sample pre-treatment is avoided. Organic solvents, for example, are not needed to extract the component of interest. Use with the small sample cell further allows volatilization and injection of vapor into the gas chromatograph, allowing for rapid detection of compounds that, using traditional methods, requires significant sample pre-treatment. The process is faster and more accurate due to avoiding a stationary phase, avoiding pre-treatment, avoiding dispersion of the sample, and use of a gas chromatograph.

The invention in another embodiment provides for improved interface lines in such devices. As discussed further below, the injector which injects the sample into the detector may itself be heated, or one can use a heated transfer line, or both. Use of a heated transfer line has several advantages in reducing condensate in the line, and avoiding false signal in subsequent sampling due to concentrate remaining in the transfer line. The cell is specifically designed for easy connections to a heated transfer line. The following is an example. Both the carrier gas in and out ports are designed for ⅛" NPT fittings. Typically the "carrier gas in" tubing consists of an ID capillary column void of any stationary phase that is connected to the alternate gas chromatograph instrument injector and flow controlled by the instrument software. The ID capillary tubing is known as "megabore" tubing and because of its larger relative diameter is ideal for sample transfer out of the column. Commonly, it is about 0.53 mm, however, this size is by no means crucial to introduce carrier gas into the cell or for it to carry sample out of the cell and enter the analytical instrument. The flow controller (whether external or internal) will ensure that the desired carrier flow "in and out" velocity, volume, and pressures are adequate for sample transfer. Alternatively, the carrier gas and flow control can be set up externally by direct coupling to a gas cylinder and flow controller. The "carrier gas out" tubing (this is the part that sweeps over the sample and carries it to the analytical instrument) is in one example simply a deactivated 0.53 mm ID fused silica capillary column (without stationary phase) that can easily be enclosed by a heated transfer line to prevent sample condensation and increase transfer efficiency. By omitting a stationary phase the analysis may occur more quickly. The transfer line connects to the cell with the ⅛" NPT fitting and inserts directly into the GC injector on the other. Due to the nature of the sample cell fittings (the ⅛" NPT is a standard thread) a variety of transfer lines can be used with the cell. The connection of lines to and from the sample cell is such that dead space and subsequent loss of the compound is minimized. A preferred embodiment provides that the transfer line is heated, which prevents condensation within the line, loss of sample and slowing of the process. See, for example, the heated transfer line described at Hannigan et al., U.S. Pat. No. 7,221,861.

Described below is the specific transfer line used in black shale and swipe (containing explosives) analysis described more fully in the example below.

LA-GC Transfer Line and Sample Cell
  2 Component system: Heated transfer line coupled to a small volume steel cell.
  GC capillary threads through transfer line and attaches directly to sample cell.
  Digital thermal controller (up to 250° C.) allows the operator to set desired temperature without a software tool pack. A digital thermal controller is a process controller. They are commercially available from Omega Engineering and it reads the temperature as measured by a thermocouple, adjusting as necessary.
  120V power The Transfer Line and Sample Cells can be integrated with any manufacturer's gas chromatograph and most laser manufacturer platforms. User controlled temperature, universal installation, and ease of use make the LA-GC Transfer Line and Sample Cell the ideal interface for analysis of organics locked in solid matrices.

Figure 2:
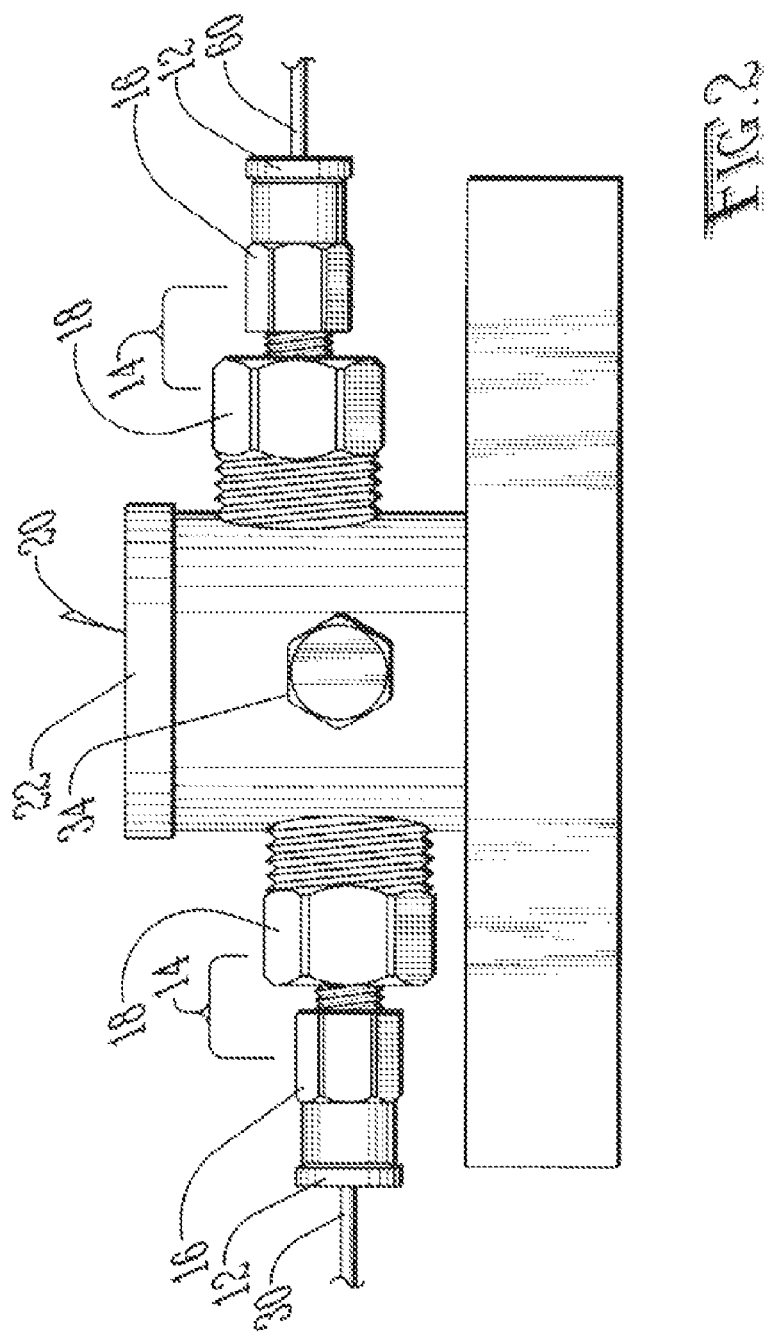
FIG. 2 is an elevated side view of interface components of a device of the invention.
Figure 3:
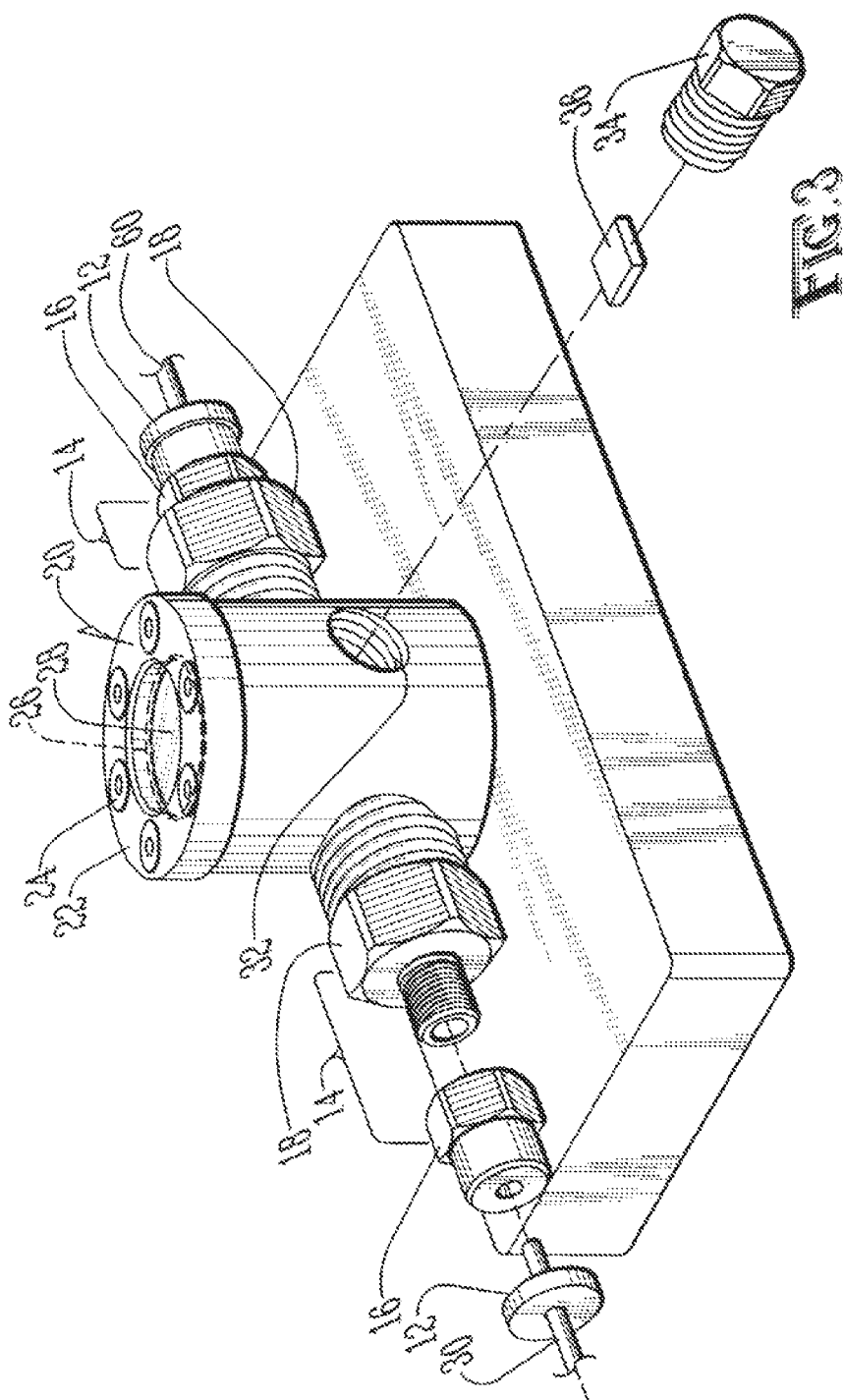
FIG. 3 is a side exploded view of the small cell and interface components of a device of the invention.

FIGS. 1-3 set forth by way of example one embodiment of a device useful in the invention. FIG. 1 shows a laser ablation system 10 with the small cell of the invention 20, here a 5 cm$^3$ steel sample cell. Leading into the sample cell is a silica transfer line 30, a capillary column without a stationary phase. This in turn is linked to a source of a carrier gas. One skilled in the art appreciates that the carrier gas can be any type of gas useful for moving the sample, such as argon or krypton. In a preferred embodiment helium is used as it is a small molecule useful in entraining components of interest in a sample. In FIG. 1 a helium tank 40 is in air flow sealed communication via tubing or the like to a helium flow controller 50. The sample cell 20 is linked by a second silica transfer line 60 that is preferably heated to a maximum of about 250° C. Heating may occur by any useful methods such as, for example, providing a nickel-chrome wire as the transfer line with voltage sent to the wire, use of a cartridge heater or the digital thermal controller, supra or the like. It is linked to the gas chromatograph 70 and mass spectrometer 80. At the interface between the GC-MS and the transfer line, in one embodiment, is an injector 90. Thus, a sample is placed in small cell2 0, and the laser initiated so that it radiates the sample with UV radiation which energizes the molecules and causes them to be volatile enough to desorb from the matrix which the compound of interest may be found. The vapor phase is increased, and an increase in the component of interest that may be present occurs in the headspace above the matrix. Helium flow control 50 is initiated so that once the vapor phase is increased, the volatile is entrained in the carrier gas and is transferred via heated transfer line 60 to injector 90. Temperature in the injector in one embodiment is maintained at about 200° C. so that what enters is in the vapor or gas phase. From there it goes into the detector. In this embodiment it is loaded on the front of the GC capillary column for separation, and is heated at a set rate. After the vapor sample is injected into the gas chromatograph 70 it is measured by the mass spectrometer 80, or a NCD as an alternative or additional measurement device. Analytical instrumentation used in examples set forth below consists of a CETAC LSX-500 solid state Nd:YAG 266 nm laser ablation system, a PerkinElmerARNEL clarus 500 gas chromatograph, a Sievers 255 Nitrogen Chemiluminescence Detector (NCD), and a PerkinElmer Clarus 500 GC-MS. To avoid column loading between analyses, one embodiment provides for a valve (in an embodiment it can be a four-way or more value) equipped with a sample loop be used which can be vented between analyses as well as just after the laser has fired. In the absence of such a valve, solvent cleanout steps can be conducted using an appropriate solvent.

FIG. 2 shows an example of a coupling system to link transfer lines to and from the cell while minimizing dead volume and reducing loss of sample. A septum 12 is used to hold the transfer line column 30 in place. The transfer line 30 is connected to the ⅛"NPT male to 1/16" compression adaptor 14 which is screwed into a ⅛" threaded port on the sample cell. The incoming transfer line 30 is inserted through a 1/16" compression nut 16 and fitted with a 1/16"×0.8 mm ID vespel/graphite ferrule. The nut 16 holding the transfer line 30 in place with the ferrule is screwed into the ⅛" NPT male to 1/16" converter 14 and tightened such that the ferrule grips the column and holds it firmly in place. A similar combination is provided exiting the sample cell 20. The other end of the transfer line 60 is simply inserted 2" (standard GC syringe needle length) into the GC injector nut 90 to complete the interface. All connections in and out of the steel sample cell are wrapped with Teflon® or other insulating tape to prevent helium carrier gas leaks. The sample cell was created with a steel base with dimensions of 2.75"×2.75"×0.75" (L×W×H) so that a hole could easily be drilled for placement of a cartridge heater for future use in pyrolysis assisted desorption studies or to enable sub-zero cell cooling by use of a peltier and cooling block for future cool cell studies.

Referring again to FIG. 1, the transfer line exiting the cell 60 is inserted about two inches through an injector nut 90. The injector nut 90 is screwed into an injector port 92 on the GC 70. The transfer line 60 passes through the injector port 92. Instead of a needle commonly used to inject fluid substances into the GC/MS, here a capillary column replaces the needle and enters through the septum. In the embodiment of FIG. 1 an external flow controller is used, but many variations are possible, and instead of the external flow control, one can use a second fused silica carrier gas line capillary leading into the sample cell with gas flow originating from the alternate GC injector, so all helium flow would be controlled by the GC instead of externally. At least one computer may be employed for precise control of the laser and GC-MS.

FIG. 3 shows detail of an embodiment of the small sample cell. Cap 22 of sample cell 20 is attached via threaded screw holes 24 with an O-ring 26 under cap 22. The center of cap 22 is fitted with a window 28. In an embodiment the window is a UV grade fused silica window with better than 95% transmission for most of the upper UV region. Carrier gas enters sample cell 20 via transfer line 30 and through the ⅛" to 1/16" converter 14. The sample cell 20 is also fitted with an inlet 32 having a ⅛" flat bottom screw 34. The screw 34 is removed in order to place the sample 36 in the sample cell 20.

Introduction of the sample can occur in any convenient method, and the invention is particularly useful in obtaining detection of a component from a solid sample. In one embodiment, PVA filter pads are cut to fit into the sample cell, and sample is added to the filter pad by dipping into the sample standard or a syringe can be used to distribute sample onto the pad. Other means of obtaining sample are available, such as, for example, swiping the suspect liquid or residue with the filter and placed into the cell. It is dried in ambient air until all solvent has visibly evaporated. Alternatively, when a solid sample is used, it may be placed intact into the cell. The sample is inserted into the sample chamber by removing the screw 34 and placing the pad or other sample matrix in the interior of the sample cell 20.

The following is presented by way of exemplification of embodiments of the invention without intending to be limiting.

EXAMPLE 1

Analytical Methods

EPA method 8095 was used for initial GC operating parameters. These parameters were altered in two ways to enhance the introduction of sample by laser desorption and to increase the speed of analysis. The normal and fast method parameters are listed below in Table 2.

TABLE 1

GC method parameters for normal and fast desorption

| Method | EPA 8095 | Normal A | Normal B | Fast A | Fast B |
|---|---|---|---|---|---|
| Injector temp (° C.) | 250 | 200 | 200 | 200 | 200 |
| Initial oven temp (° C.) | 100 | 30 | 50 | 65 | 40 |
| Hold time 1 (minutes) | 2 | 0 | 0 | 0 | 0 |
| Rate 1 (° C./min) | 10° C./min to 200° C. | 15 | 20 | 40 | 45 |
| Rate 2 (° C./min) | 20 | 0 | 0 | 0 | 0 |

TABLE 1-continued

GC method parameters for normal and fast desorption

| Method | EPA 8095 | Normal A | Normal B | Fast A | Fast B |
|---|---|---|---|---|---|
| Final oven temp (° C.) | 250 | 150 | 150 | 140 | 140 |
| Hold time 2 (minutes) | 0 | 0 | 0 | 3.125 | 2.78 |

An assortment of laser parameters such as energy level, frequency of pulses, number of pulses, and spot size, were explored. It was found that using the "preferred" parameters indicated below in Table 3 produced adequate NCD response with little, if any, resulting ablation of the sample swipe matrix. The energy values supplied by the manufacturer were different than measured energies and these measured energies were used for all calculations. Limiting the amount of ablation is important in that particulate matter can clog GC capillary columns and reduce NCD sensitivity by coating the walls of the ozone reaction chamber and pre-detector filters.

TABLE 2

Laser ablation parameters employed for maximum desorption by Nd: YAG 266 nm laser

| Parameters | Default Energy | Intermediate Energy | Preferred Energy |
|---|---|---|---|
| Energy (mJ) | 100% (9 mJ) | 70% (6.3) | 50% (4.5) |
| Measured Energy (mJ) | 3.1 | 1.4-1.7 | 0.7-1.0 |
| Fluence (J/cm$^2$) | 29 | 20 | 14 |
| Fluence Measured (J/cm$^2$) | 10 | 4.5-5.0 | 2.0-3.0 |
| Irradiance (W/cm$^2$) | $5.0 \times 10^9$ | $3.3 \times 10^9$ | $2.4 \times 10^9$ |
| Irradiance Measured (W/cm$^2$) | $1.6 \times 10^9$ | $7.0 \times 10^8$-$9.0 \times 10^8$ | $3.7 \times 10^8$-$5.3 \times 10^8$ |
| Frequency (Hz) | 20 | 15 | 10 |
| Pulses | 200 | 20 | 10 |
| Spot size (μm) | 150 | 200 | 200 |

EXAMPLE 2

Analysis of Black Shale

An in situ analytical method for the detection and characterization of organic matter in black shales was shown. Black shale is a limited source for oily hydrocarbons generated from the processes of diagenesis and catagenesis.

As an alternative to the existing standard operating procedures for organic analysis, the above-described sample cell and laser ablation-gas chromatograph (LA-GC) instrument interface was designed to deliver ideal sample volumes and transfer efficiencies necessary for analysis by GC-MS. GC has been used for many decades in successful separations of a wide range of compounds derived from many types of samples and mass spectrometer detectors are excellent for analysis of organic compounds because they are compound specific and can provide unambiguous identification of the constituents in a sample. Here, LA-GC with mass spectrometry (MS) expected to show direct sampling of the black shale matrix which would dramatically save analysis time by eliminating the need for tedious extraction steps and to characterize volatile organic materials stored in black shale source rocks. It was determined that by changing ablation parameters such as energy, pulse repetition rate, and bursts, the system effectively and efficiently desorbed organic compounds and introduced these volatilized compounds into the GC. Also investigated was in-injector pyrolysis as an alternative to the pyrolysis cell typically interfaced to a GC-MS. Both in-injector pyrolysis and the LA-GC interface were efficient sample introduction methods allowing for characterization of organic matter in solid samples while by-passing traditional extraction procedures. Details are set forth below Instrumentation and Interface (LA-GC-MS)
Laser Ablation System—CETAC LSX-500

| Wavelength | 266 nm |
|---|---|
| Energy range | 1.5-9 mJ (5-100%) |
| Spot sizes | 10-200 μm |

The 266 nm is a sufficient wavelength for thorough ablation of most colored and colorless solid materials (Jackson, 2001).

Perkin Elmer Clarus 500 GC-MS
Temperature programmable—oven, injector, and detector, carrier gas flow rate, timed events

| MS Mass Range | 35-600 Da |
|---|---|
| EI Source | 70 eV |
| Selected Ion Mode | |
| NIST Reference Library | |

GC capillary column 30 meter, 0.25 mm inner diameter, 0.1 mf DB-5

A 5 cm³, low volume sample cell was designed and constructed for this study to achieve appropriate sample introduction into the GC.

Interface Components
3 meter, 0.53 mm inner diameter fused silica transfer column with no stationary phase
5 cm³ sample cell
GC injector The fused silica transfer line is connected to the sample cell using a ⅛" to ¹⁄₁₆" steel converter.
The other end of the transfer column is inserted 2 inches through the septum in the injector nut.
Glass wool is placed into the injector liner to prevent particulate matter from entering the GC column.

Sample Preparation

Black shale pellets are made using a steel nut with a ⅛" threaded inner diameter. The black shale powder is placed in the nut and flat bottom screws are tightened around the powder to compress it into a pellet. This pellet is placed into the sample cell. Extracted bitumen is prepared for laser sampling by placing a small amount onto a slide. The slide is placed into the sample chamber. Bitumen samples for direct injection GC-MS analysis were prepared by dissolving 3 mg into 20 mL of hexane to create a solution of 150 ppm.

LA-GC-MS Method Parameters

| Laser Energy | 50% (4.5 mJ) |
|---|---|
| Pulse Frequency | 10 Hz |
| Pulse Number | 10 shots |
| Spot size | 200 mm |
| Oven Program | |
| Initial Temperature | 40° C. hold 1 min |
| Hold Time 1 | 1 minute |
| Oven Ramp | 5° C./minute |
| Final Temperature | 280° C. |
| Hold Time | 2-11 minutes |
| Injector Program | |
| Temperature | 250° C. |
| Flow Rate 1 | External 2 mL/min flow (Removed after 1 minute) |
| Flow Rate 2 | 1 mL/min (Applied at 1 minute) |
| Split | 20:1 (Applied at 1.01 minute) |

Results

Figure 4:
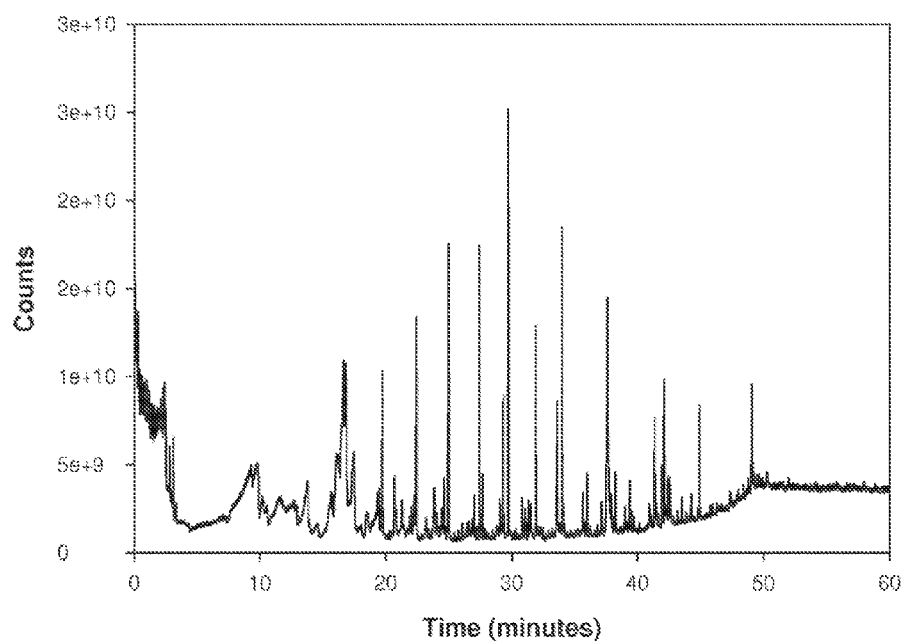
FIG. 4 shows an LA-GC-MS chromatogram of organics in black shale obtained by direct laser desorption.
Figure 5:
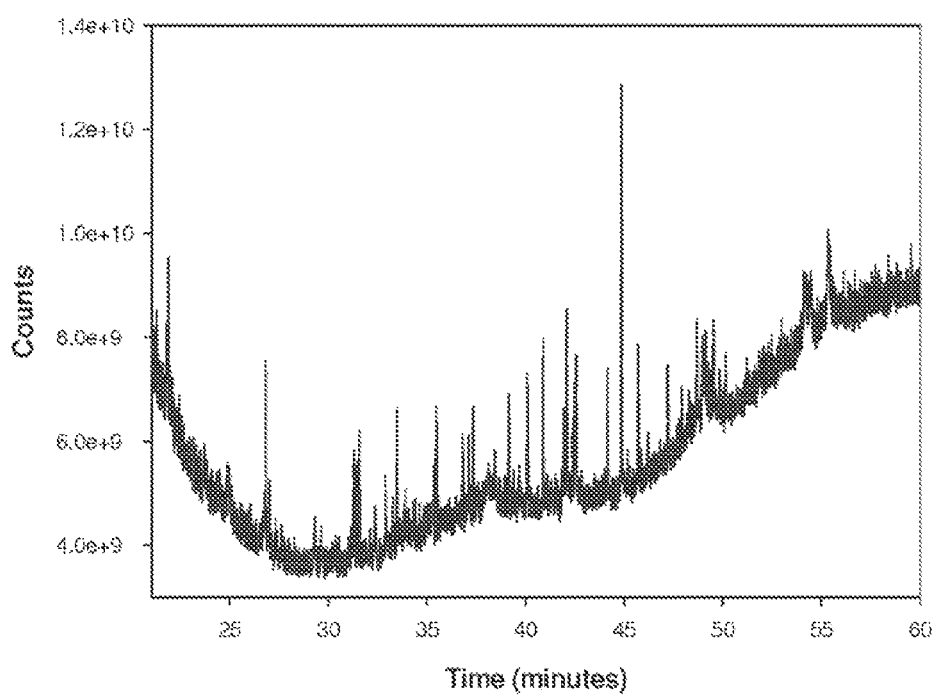
FIG. 5 is a GC-MS chromatogram of extracted bitumen obtained by direct injection.
Figure 6:
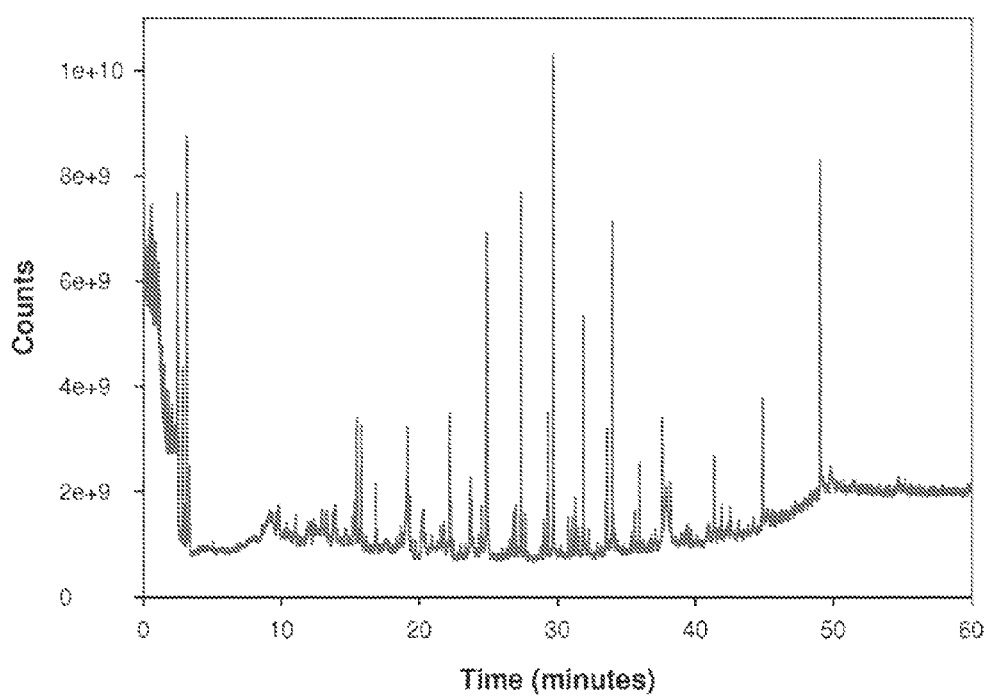
FIG. 6 is a LA-GC-MS chromatogram of extracted bitumen obtained by direct laser desorption.

FIG. 4 shows a LA-GC-MS chromatogram of organics in black shale obtained by direct laser desorption. FIG. 5 is a GC-MS chromatogram of extracted bitumen obtained by direct injection. FIG. 6 is an LA-GC-MS chromatogram of extracted bitumen obtained by direct laser desorption. The LA-GC-MS chromatograms using direct laser sampling of black shale pellets and bitumen reveal an assortment of alcohol, aldehyde, ketone, alkane, and alkene peaks with carbon content ranging from $C_{10}$ to $C_{20}$. GC-MS analysis of bitumen by direct injection produces poorer resolution of compounds. Nearly all compounds were identified as alkanes and alkenes. Signal to Noise ratios were greatly enhanced using the laser sampling technique. S/N=150, 180, and 66.5 for tallest peak in FIGS. 4, 6, and 5 respectively.

| | Compound | Retention Time (minutes) - Black Shale | Retention Time (minutes) - Bitumen |
|---|---|---|---|
| A | Undecanal (C11) | 19.72 | 19.15 |
| B | Dodecanal (C12) | 22.43 | 22.18 |
| C | Tridecanal (C13) | 24.99 | 24.88 |
| D | Tetradecanal (C14) | 27.41 | 27.36 |
| E | Tetradecanal (C14) | 29.71 | 29.69 |
| F | Hexadecanal (C16) | 31.90 | 31.89 |
| G | Tetradecanal (C14) | 33.98 | 33.97 |
| H | 1-Eicosanol (C20) | 37.61 | 37.60 |
| I | Squalene (C30) | 49.04 | 49.02 |

In conclusion, the LA-GC-MS interface effectively and efficiently desorped organic compounds and introduced these volatilized compounds into the GC. The small volume sample cell was appropriate for sample transfer into GC. When combined with laser desorption, injector temperature of 250° C. is adequate for in-injector pyrolysis as an alternative to the pyrolysis cell typically interfaced to a GC-MS. Laser desorption is an efficient sample introduction method allowing for characterization of organic matter in solid samples while by-passing traditional extraction procedures.

EXAMPLE 3

LA-GC-NCD Interface Used to Detect Components of Explosive Compounds

Detection of explosive components is shown using an interface of a laser ablation system with a gas chromatograph equipped with either a Nitrogen Chemiluminescence Detector (NCD) or Mass Spectrometer (MS) for sensitive and selective detection of explosives concentrated on a sample swipe matrix. By varying specific parameters such as energy level, pulse frequency, bursts, and spot size, the 266 nm UV laser was proven to be adequate for sample introduction of explosives when a low volume sample cell was employed. Selective and sensitive detection of TNT derivatives was achieved with both the nitrogen specific NCD and with the MS. Selectivity of the MS was enhanced by using the Selective Ion Mode (SIM). The MS was used primarily to confirm the identity of GC-NCD chromatographic peaks as well as to verify desorption of total explosive molecules by the laser.

Other than peroxide based explosives, most of the commonly implemented primary and secondary explosives such as TNT, RDX, PETN, and several explosive mixtures contain nitrogen in the form of amines, nitro, or nitrate functional groups. Due to these nitrogen groups, one such selective detection technology is the Nitrogen Chemiluminescence Detector (NCD). A Nitrogen Chemiluminescence Detector, which detects only nitrogen, employs a high temperature burner (700° C.) for pyrolysis of nitrogen in the compound. By high temperature pyrolysis the nitrogen in the sample is converted to nitric oxide (NO), which is then passed to a low pressure ozone reaction chamber where reaction with excess ozone converts NO to an electronically excited nitrogen dioxide ($NO_2^*$) as seen in the following reaction:

$$NO + O_3 \rightarrow NO_2^+ + O_2 \qquad \text{eqn. 1}$$

As the electronically excited $NO_2^*$ relaxes back to the ground state, a photon is emitted as shown in the reaction below:

$$NO_2^+ \rightarrow NO_2 + h\nu \qquad \text{eqn. 2}$$

The chemiluminescent photon emission occurs in the visible and near-infrared region of the electromagnetic spectrum and is centered on 1200 nm. Yan (2002). The photon emission is detected using a photomultiplier tube (PMT). NCD is ideal because the emitted light detected by the PMT is proportional the NO* concentration and hence to the original nitrogen content of the N-containing compound. The $NO/O_3$ measurement has been shown to be very sensitive and linear over several orders of magnitude, provided that good operating parameters are maintained ($O_3$ concentration, reaction chamber pressure, stable vacuum) and the PMT and optical filter employed are optimized for the chemiluminescent reaction. Nyarady (1985); Yan (1999). Furthermore, only the total chemically bound nitrogen is detected as the atmospheric nitrogen is not converted to NO during the reaction process. (Yan 2002). When used in conjunction with a carbon and oxygen detector such as a Flame Ionization Detector, the unique N % (NRC (2004)-2) in the molecular formula could be used to discriminate the compound of interest (COI) from other N containing interferents such as fertilizers, diesel exhaust, and combustion products from the combustion of fossil fuels.

Before a detector such as the NCD can be employed, an effective sampling mechanism must be available. The goal here is to effectively sample the vapors emitted by the manufacture of explosives or from the explosive device itself. This is possible because vapor plumes are emitted from the weapons due to high vapor pressures and persist in the troposphere, leaving trace amounts that are detectable with sensitive instrumentation. Explosives however, have a range of vapor pressures (Table 3). This means that vapor sampling devices may be applicable to some explosives but their sensitivities are diminished for others such as PETN and HMX. However, many explosive residues adhere well to a variety of surfaces, (Pinnaduwage (2003)) making some type of vapor and particulate desorption method ideal for explosive detection.

TABLE 3

List of properties of some explosives

| Chemical name | Abbreviation | Class | Molecular Weight | Vapor pressure at 25° C. (Torr) |
| --- | --- | --- | --- | --- |
| 2,4,6-Trinitrotoluene | TNT | Nitroaromatic | 227.13 | $5.8 \times 10^{-6}$ |
| 2,6-Dinitrotoluene | DNT | Nitroaromatic | 182.14 | $1.1 \times 10^{-4}$ |
| 2,4-Dinitrotoluene | DNT | Nitroaromatic | 182.14 | $1.1 \times 10^{-4}$ |
| 3,4-Dinitrotoluene | DNT | Nitroaromatic | 182.14 | $1.1 \times 10^{-4}$ |
| Pentaerythritol tetranitrate | PETN | Nitrate ester | 316.15 | $3.8 \times 10^{-10}$ |
| 1,3,5-Trinitro-1,3,5,7-triaza-cyclohexane | RDX | Nitramine | 222.12 | $4.6 \times 10^{-9}$ |
| 1,3,5,7-Tetranitro-1,3,5,7-tetrazacyclooctane | HMX | Nitramine | 296.16 | $1.6 \times 10^{-13}$ |

As mentioned above, lasers are frequently incorporated into technologies for detection of explosives. One useful laser method is laser desorption which is used for desorbing explosives from a variety of matrices. Alexander (1993). Morgan et al., (1999) found that an infrared, pulsed $CO_2$ laser can dramatically raise the temperature of explosive containing substrates such as soil, thereby increasing the vapor pressure and detection thresholds two or more orders of magnitude. Morgan (1999). While lasers operating in the infrared are often used for desorption studies with instruments like the MALDI-TOF, (Vorm (1994)) ultraviolet lasers may prove to have some desorption utility for explosives. This is evidenced by the strong absorption coefficients of benzene, cyclohexane, and toluene (common backbone structures of several explosives) in the ultraviolet region, particularly around 275-285 nm. Lide (1995). This is important because if the laser pulse is absorbed and low enough energies are used, ablation can be avoided and the explosive materials can be evaporated from the matrix (due to rapid heating) before energy is distributed to the internal degrees of freedom. Weickhardt (2003). As a means for development and evaluation of an ultraviolet laser for desorption, a Cetac LSX-500 Nd:YAG 266 nm laser ablation system is used here at a reduced energy of 50%.

The laser produced by this system is a stable, multimode laser meaning there is a superposition of many TEM (Transverse Electromagnetic Modes—cross sectional shape of the beam) modes instead of only one running mode which leads to equal energy density across a transverse cross-section of the beam. Polyvinyl acetate (PVA) bound glass filter pads are used as the sample matrix for an assortment of explosive standards. As shown by Yinon and Zitrin (1993), an interaction resulting from contact with the beam, specifically the heat energy delivered to the explosive, is an increase in vapor phase by the compound, followed by an increase in the concentration of the explosive in the headspace above the matrix. Yinon (1993). As described above, laser induced breakdown spectroscopy (LIBS) is one manner of sampling this vapor plume of sample by using a spectrographic detector. Another method is to use a laser to create a desorbed vapor plume above the original matrix and entrain the vapor in an inert gas such as helium and carry it to a separation and detection instrument such as the GC-NCD or some other analytical instrument of choice.

One drawback to the exclusive use of a NCD is that the detector is only sensitive to nitrogen and other types of explosives such as the peroxide based TATP (triacetonetriperoxide) will not be detected. Another drawback is that, as with many detectors (FID, ECD), standards are the primary means for identification of COI's in samples. For this reason, as well as a means for verification of compounds detected by the NCD, a GC-MS equipped with a NIST mass spectra library is employed in this research. Mass spectrometry is described above. Along with the NCD, if a mass spectrometer employing a NIST library search of mass spectral information is added to the interface, a method of orthogonal detection can be established that will provide additional levels of quality control and identification of COI's.

The goal of this research was to construct an interface between a laser ablation system and a gas chromatograph equipped with a nitrogen chemiluminescence detector for fast and reliable detection of explosives on a sample swipe matrix. In order to accomplish this goal, two primary problems had to be addressed. First, an appropriate sample swipe material had to be chosen which could adequately store explosive samples loaded onto it and be free from other sources of nitrogen which could lead to errors and otherwise interfere with chemiluminescence detection upon partial ablation. Secondly, a sample cell of an appropriate volume for introduction into a gas chromatograph had to be devised and constructed. Polyvinyl acetate (PVA) bound glass filter pads were used previously to collect tobacco smoke. Elobeid (2005). and were also found to be appropriate for use here as a negligible nitrogen signal was obtained in blank samples and explosive compounds could be loaded onto the filter pad and detected many hours later. To resolve the second problem, the 250 cm$^3$ manufacturer provided laser ablation sample cell was replaced with a custom designed 5 cm$^3$ steel sample cell equipped with an 1/8"NPT male to 1/16" compression adaptor at the inlet and outlet for easy connection to a fused silica capillary transfer column. One obvious drawback to using a metal sample cell is that explosive materials may adhere to the cell walls when left unheated. Yinon (1993). For this reason, a vinyl backed FEP fluoropolymer surface protector from Bytac was used to line the inside of the cell to create inert surfaces where little, if any, compound-cell surface interactions would occur. The sample cell is equipped with a UV grade fused silica window with better than 90% transmission in the ultraviolet region. Unfortunately, the need for a heated transfer line was only realized upon near completion of a large portion of sample analysis but the absence of a stationary phase on the fused silica transfer line nevertheless allowed for adequate sample transfer for analysis.

A secondary problem that had to be addressed was the choice of an appropriate GC capillary column for evaluation of performance of the novel instrument interface. This research employed a Restek Rtx-TNT 2 capillary column. This column is prepared with a proprietary stationary phase that allows high thermal stability and good resolution of explosive compounds. The column was specifically designed for identification of 16 explosive analytes listed in the US EPA Method 8095 which was a method used as starting point for gas chromatograph parameters. A 6 meter, 0.53 mm ID megabore column was used for all NCD analysis while a 15 meter, 0.25 mm ID was used for MS analysis. In order to evaluate the capillary column, 1000 ppm standards of TNT and its DNT derivatives were purchased from Cerilliant. The standards were used to build calibration curves both by direct injection and laser desorption. The analytical and method parameters used in this study are shown in Table 2 above.

Results 1,5-dinitrotoluene

Figure 7:
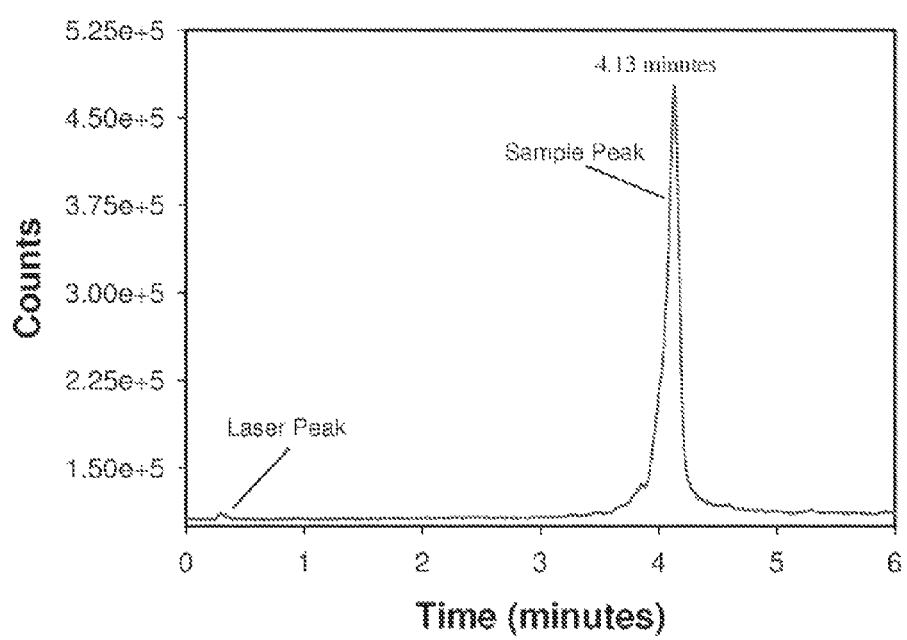
FIG. 7 is a LA-GC-NCD chromatogram for 50 ppm 2,6-dinitrotoluene.
Figure 8A:
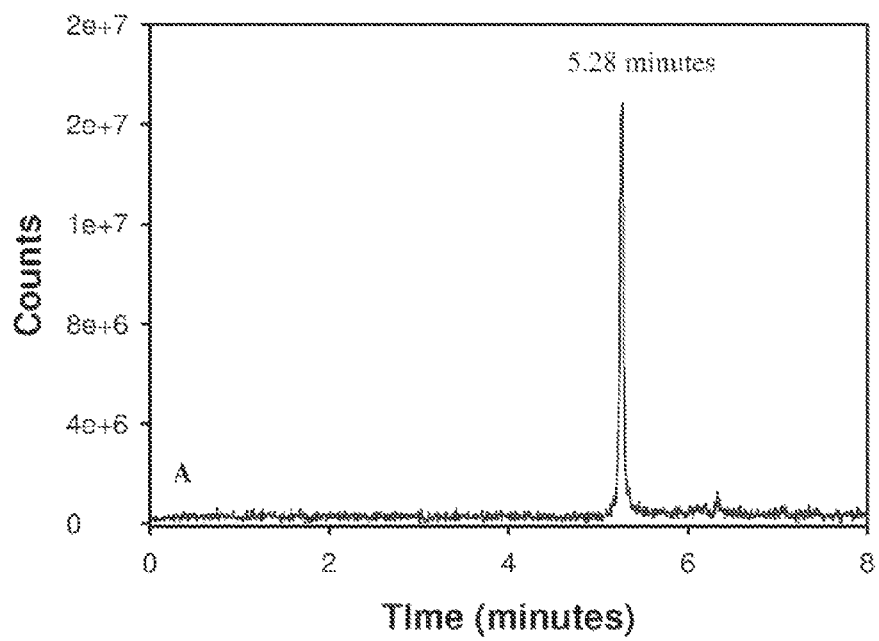
FIGS. 8A and 8B are LA-GC-MS chromatograms for 50 ppm 2,6-dinitrotoluene using both SIM (A) and TIC (B) modes.
Figure 8B:
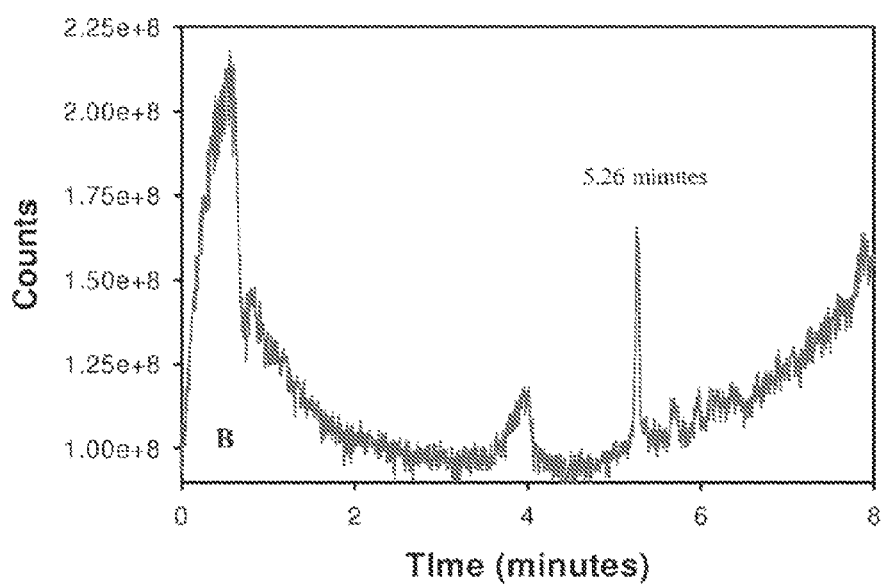

Two peaks are present in LA-GC-NCD analysis of 50 ppm 2,6-dinitrotoluene (FIG. 7). The first peak is obtained almost instantaneously after the laser is fired. After confirmation with the LA-GC-MS interface, the second peak at 4.1 minutes was identified as 2,6-dinitrotoluene (FIGS. 8A and 8B). The identity of the sample peak (FIG. 8A) was determined by using the NIST library database to compare the spectrum of the chromatographic peak which was isolated using selected ion monitoring (SIM) mode. SIM is used to make the chromatogram and subsequent library search more selective by entering the most abundant fragment ions characteristic of the particular compound. Total ion count (FIG. 8B) on the other hand, shows the chromatogram obtained with every ion detected by the mass spectrometer and as such is not selective to any one molecule's characteristic fragment ions. Both the chromatograms were obtained using the GC method "Normal B" described in Table 2 except for the additional 1 minute hold time at the final temperature that was applied to the mass spectrometry analysis. The difference in retention times between the GC-NCD and GC-MS chromatograms are due to the use of a longer, 15 meter, 0.25 um inner diameter TNT2 column which was needed to establish the necessary vacuum ($10^{-6}$ Torr) required by the mass spectrometer.

Acetonitrile

A filter pad left blank (0-8 minutes) and loaded (19-27 minutes) with acetonitrile (solvent for explosive standards) was analyzed with the LA-GC-NCD interface (FIG. 9) using various pulse frequencies and numbers (shots). An increase in signal is obtained when the filter is loaded with acetonitrile (19-27 minutes) but this increase is not appreciable when an explosive analyte is added to the filter (FIG. 7). The higher signal is likely due to residual traces of the nitrogen inclusive solvent (acetonitrile) on the filter pad. In addition, all peak signals increased as pulse frequency and number of shots increased meaning that the detector was possibly experiencing an increase in electromagnetic interference.

When a frequency of 20 Hz and 50 or more shots were used, the beam ablated completely through the filter pad which was undesirable for the goal of desorption. When 10 shots were fired at a frequency of 10 Hz, the amount of ablation was greatly diminished. These laser parameters were found to be preferred for abundant sample intensity with little, if any, ablation and were used for all analyses (See Table 2 above).

Example

Shortening Analysis Time

Figure 10A:
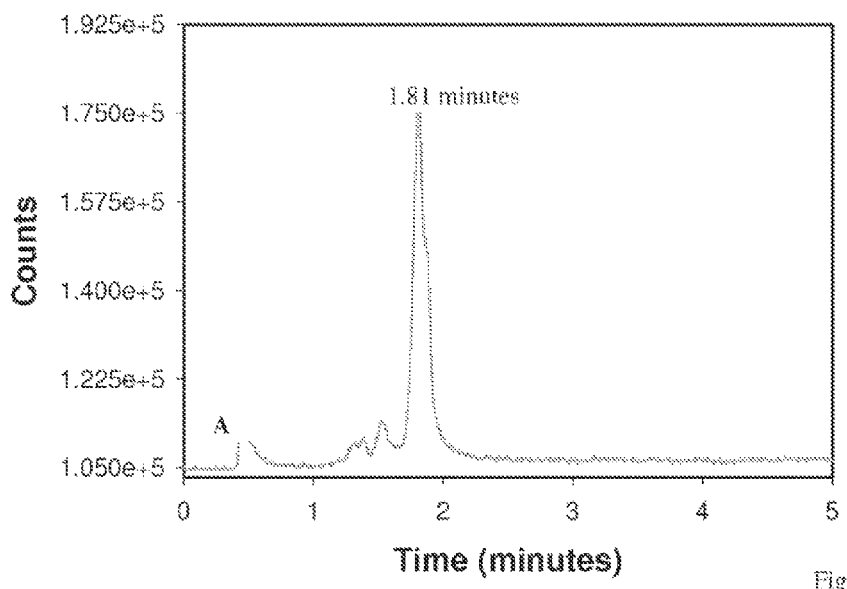
FIGS. 10A and 10B are LA-GC-NCD chromatograms of 50 ppm 1,2-dinitrobenzene obtained using "Fast Method B" (A) "Normal Method B" (B).
Figure 10B:
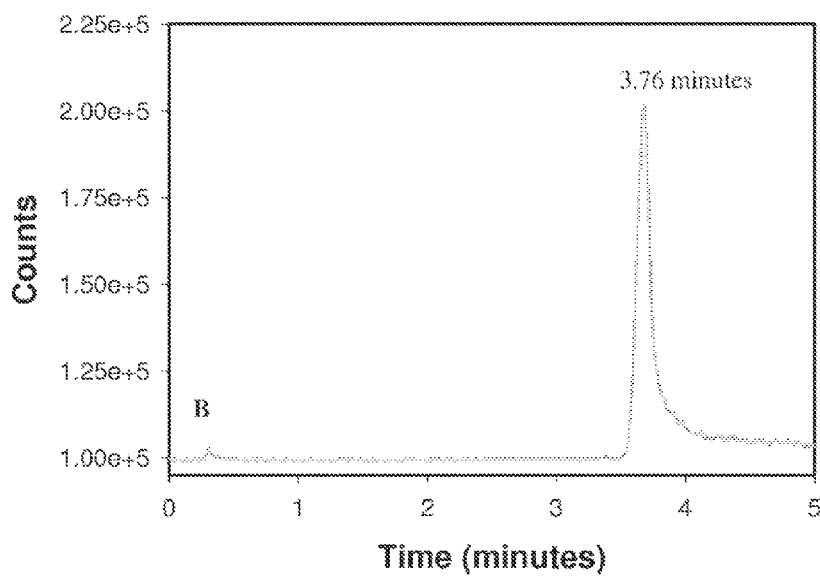
Figure 11A:
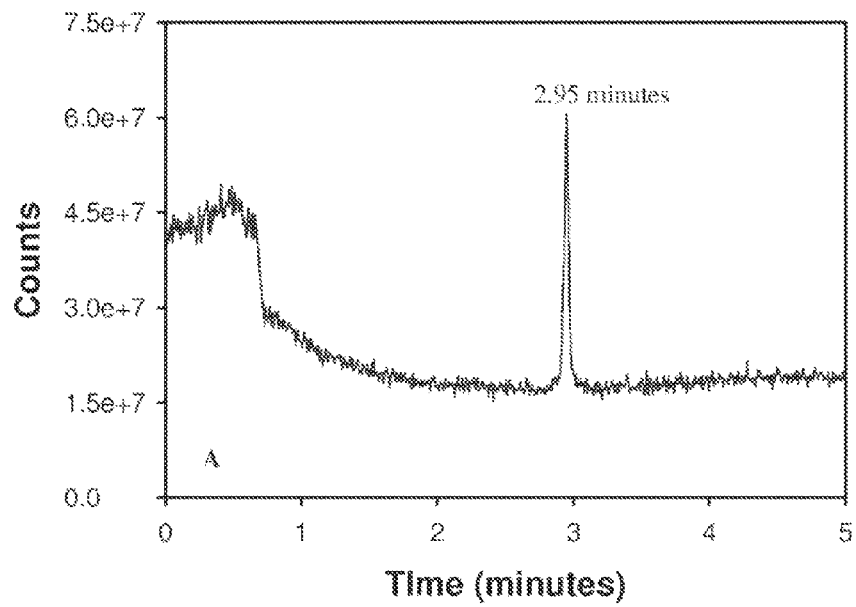
FIGS. 11A and 11B is LA-GC-MS chromatograms of 50 ppm 1,2-dinitrobenzene using SIM (A) and TIC (B) obtained using "Fast Method B".
Figure 11B:
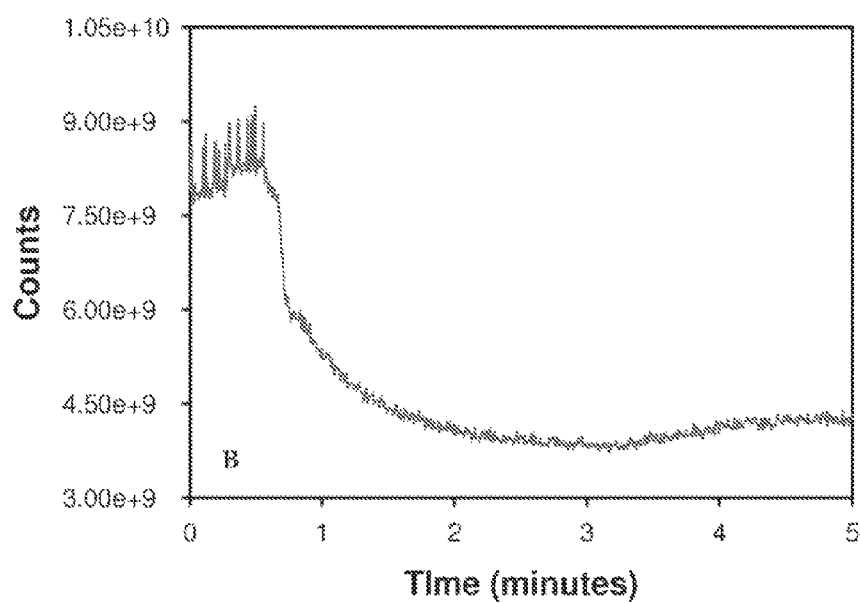
Figure 15A:
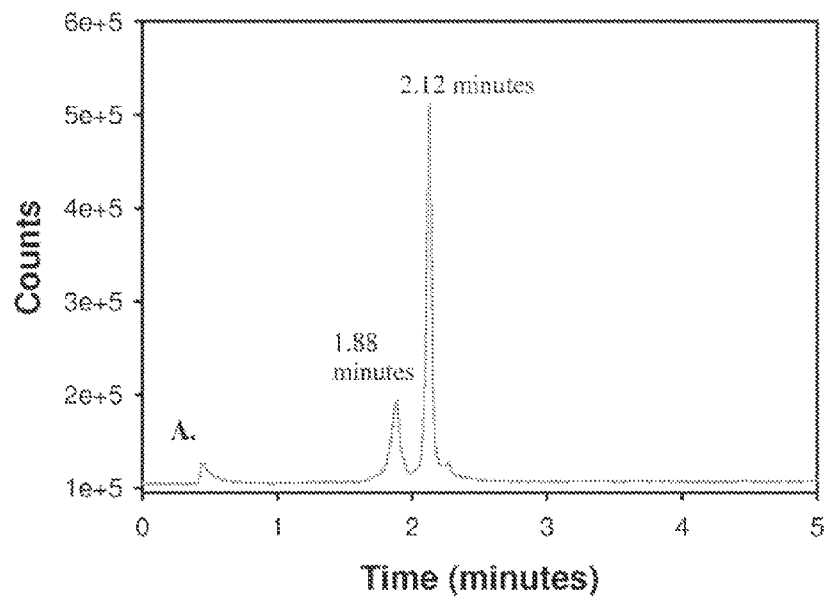
FIGS. 15A and 15B are LA-GC-NCD 50 ppm 2,4-dinitrotoluene chromatograms obtained using fast (A) and normal (B) methods.
Figure 15B:
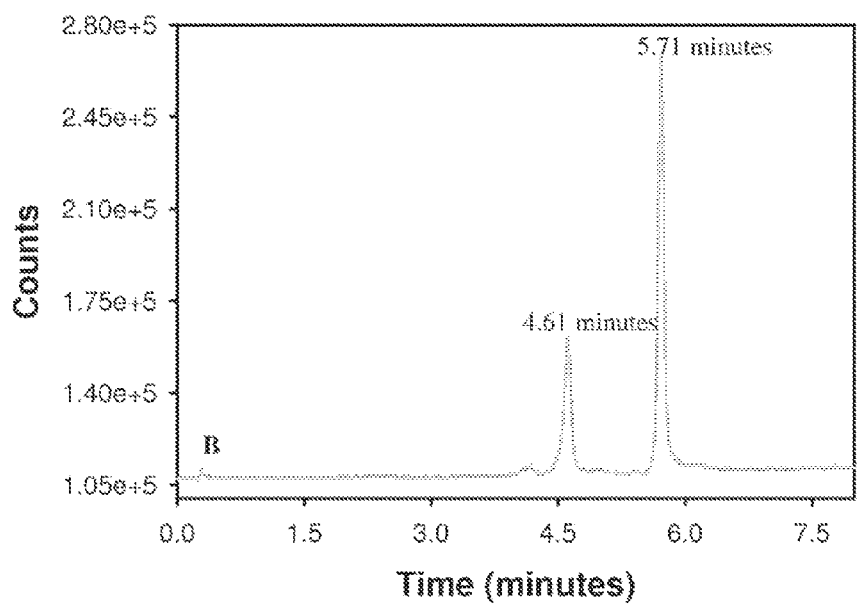
Figure 16A:
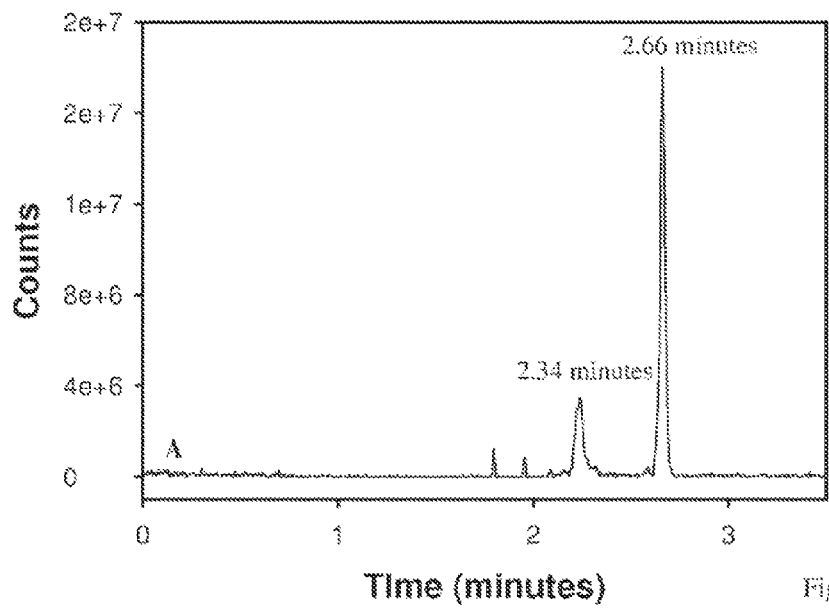
FIGS. 16A and 16B are LA-GC-MS 50 ppm 2,4-dinitrotoluene SIM chromatograms obtained using "Fast" and "Normal" methods for A and B respectively.
Figure 16B:
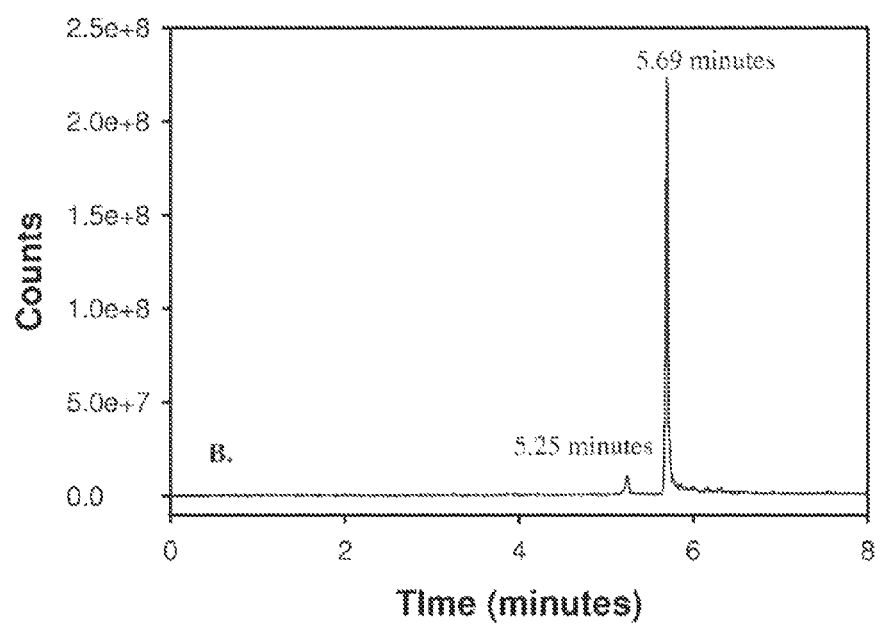

The method can be changed to shorten analysis time of several explosives with both the LA-GC-NCD and LA-GC-MS interfaces. LA-GC-NCD analyses of 1,2-dintirobenzene, 1,3-dinitrobenzene, and 2,4-dinitrotoluene were conducted using both the "Fast Method B" and the "Normal Method B" described in Table 2 for 50 ppm concentrations of each compound (FIGS. 10, 13, 15). Conformation of the peaks detected by NCD for both fast and normal analysis was achieved using identical GC methods with the LA-GC-MS (FIGS. 11, 12, 14 and 16). A NIST library spectrum search was conducted for each sample peak (in green-top) after isolation using SIM mode (Table 4).

TABLE 4

Specific ions used for SIM to isolate explosives from total ion count (TIC)

| Compound | Ions Chosen for Selected Ion Monitoring (m/z) |
|---|---|
| 2,6-dinitrotoluene | 63, 89, 165, 182 |
| 1,2-dinitrobenzene | 30, 50, 63, 168 |
| 1,3-dinitrobenzene | 30, 50, 76, 92, 122, 168 |
| 2,4-dinitrotoluene | 63, 89, 165, 182 |
| 3,4-dinitrotoluene | 30, 63, 89, 182 |

Figure 17:
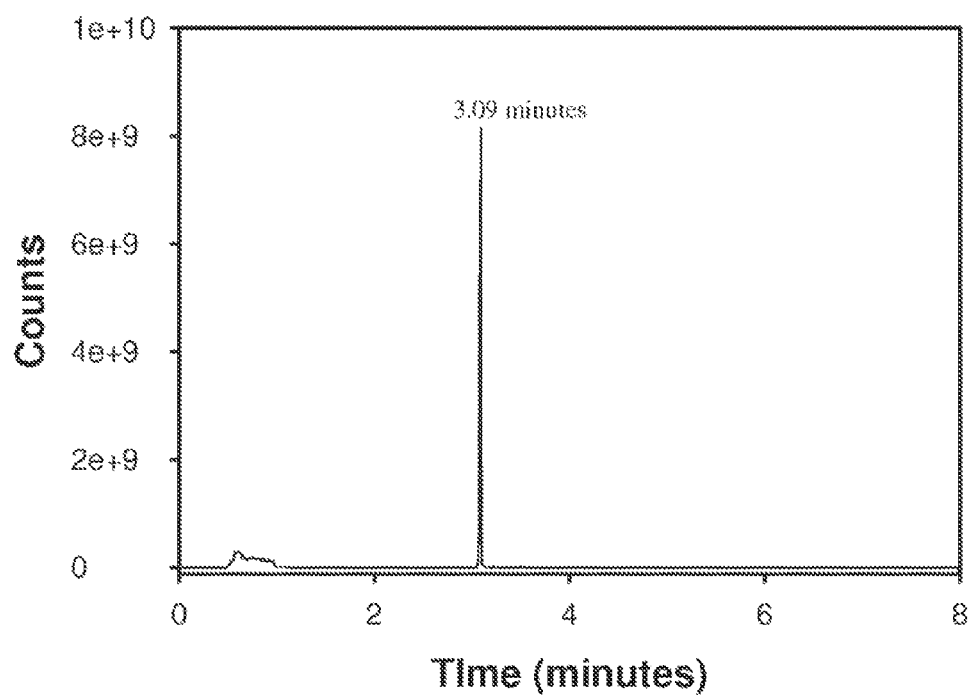
FIG. 17 is a GC-MS chromatogram of 2,4-dinitrotoluene obtained using sample introduction by direct injection.

It is interesting to note that analysis of 2,4-dinitrotoluene with both the LA-GC-NCD (FIG. 15) and LA-GC-MS (FIG. 16) produces two chromatographic peaks. The second chromatographic peak (5.69 minutes—FIG. 16B) was identified using a NIST library search of the peak's corresponding GC-MS spectrum with 77.6% match probability as 2,4-dinitrotoluene. A subsequent NIST library search of the GC-MS spectrum produced by the first peak identified it as 2,6-dinitrotoluene with a probability of 37.2%. The appearance of this first peak (5.25 minutes—FIG. 16B), obtained using two different detectors, is likely a laser induced fragmentation or degradation peak. This is evidenced by the presence of only one peak (FIG. 17) when direct injection is used as the GC-MS sample introduction method.

Figure 12:
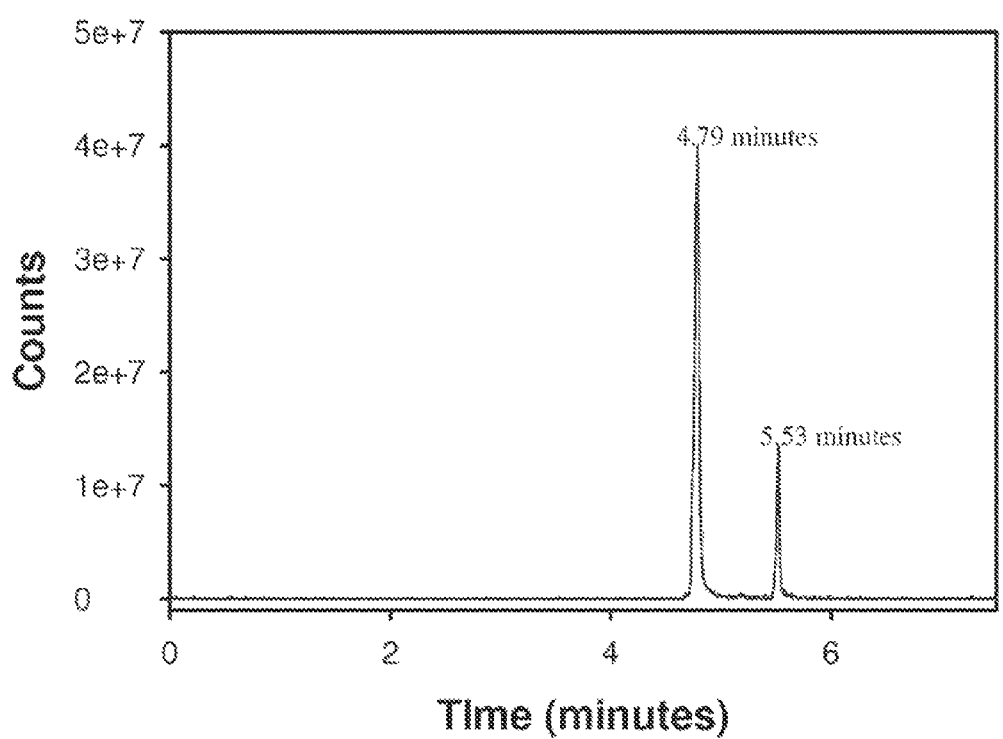
FIG. 12 is a LA-GC-MS 50 ppm 1,2-dinitrobenzene SIM chromatogram obtained using "Normal Method B".
Figure 13A:
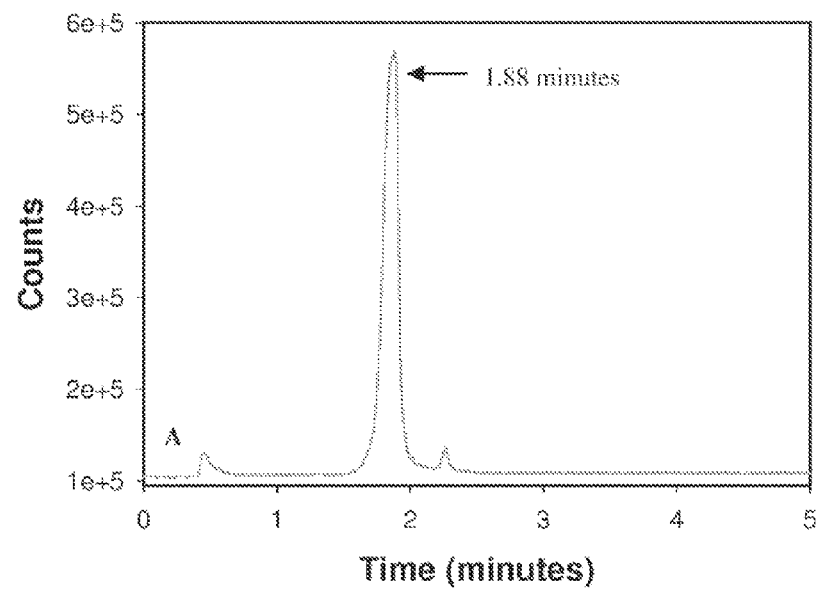
FIGS. 13A and 13B are LA-GC-NCD 50 ppm 1,3-dinitrobenzene chromatograms obtained using "Fast" (A) and "Normal" (B) methods.
Figure 13B:
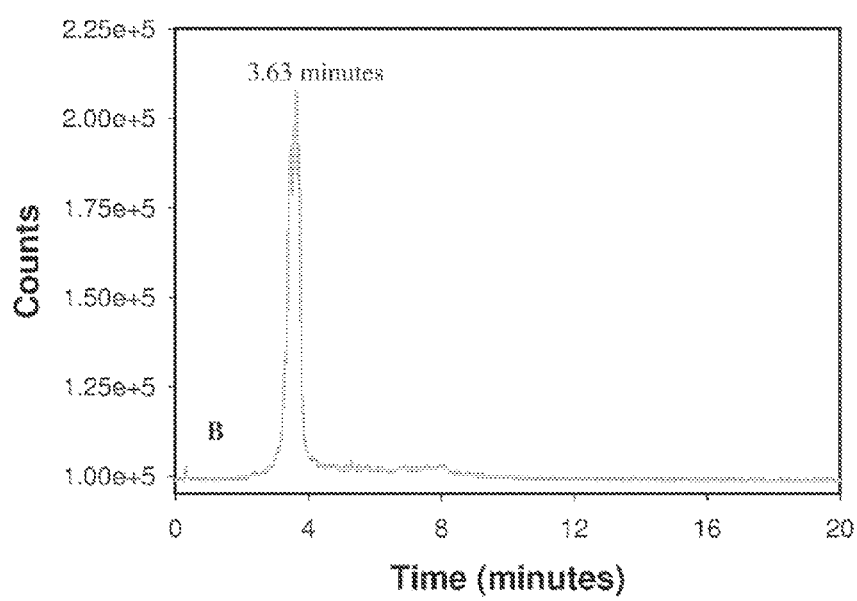
Figure 14A:
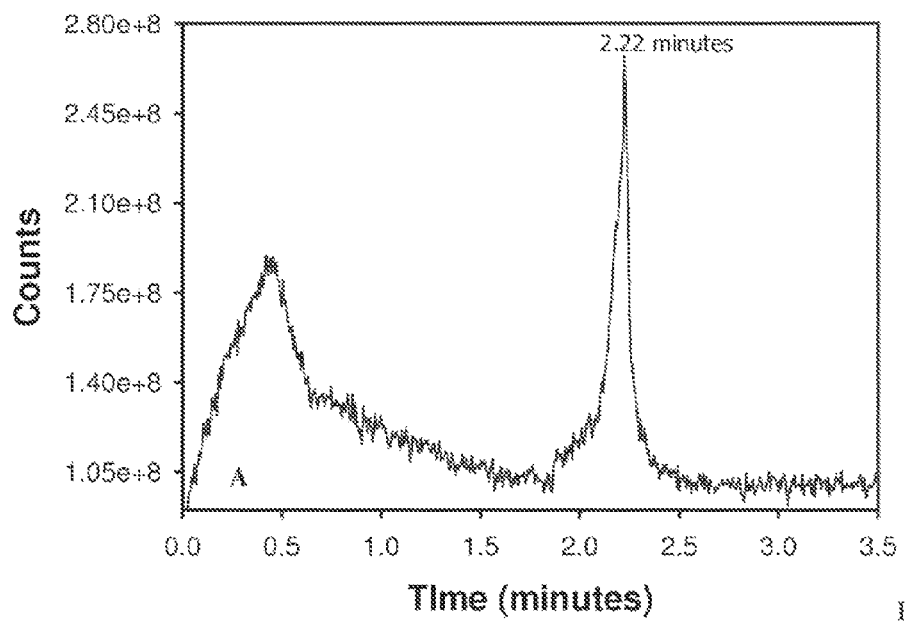
FIGS. 14A and 14B are LA-GC-MS 50 ppm 1,3-dinitrobenzene chromatograms obtained using SIM modes. The chromatograms were obtained using "Fast" and "Normal" methods for A and B respectively.
Figure 14B:
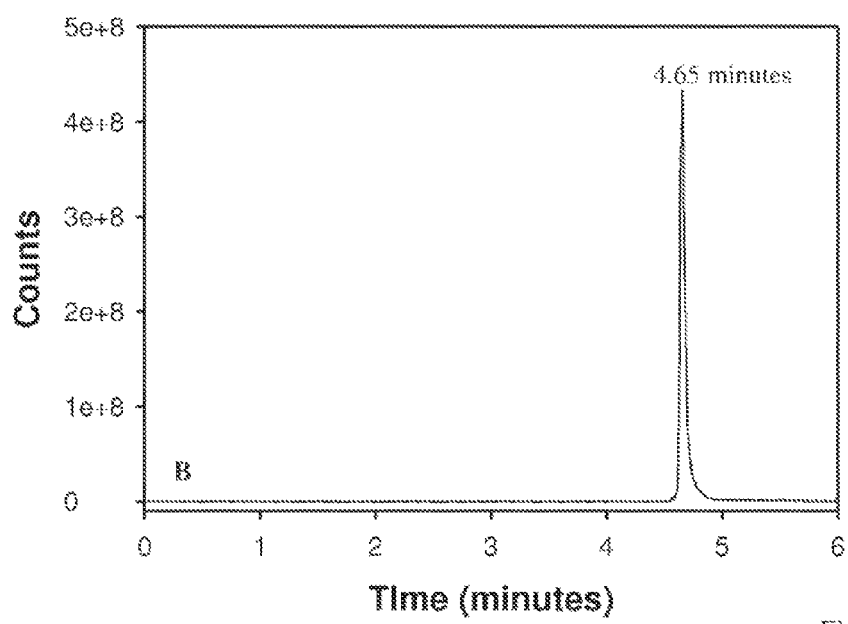
Figure 18:
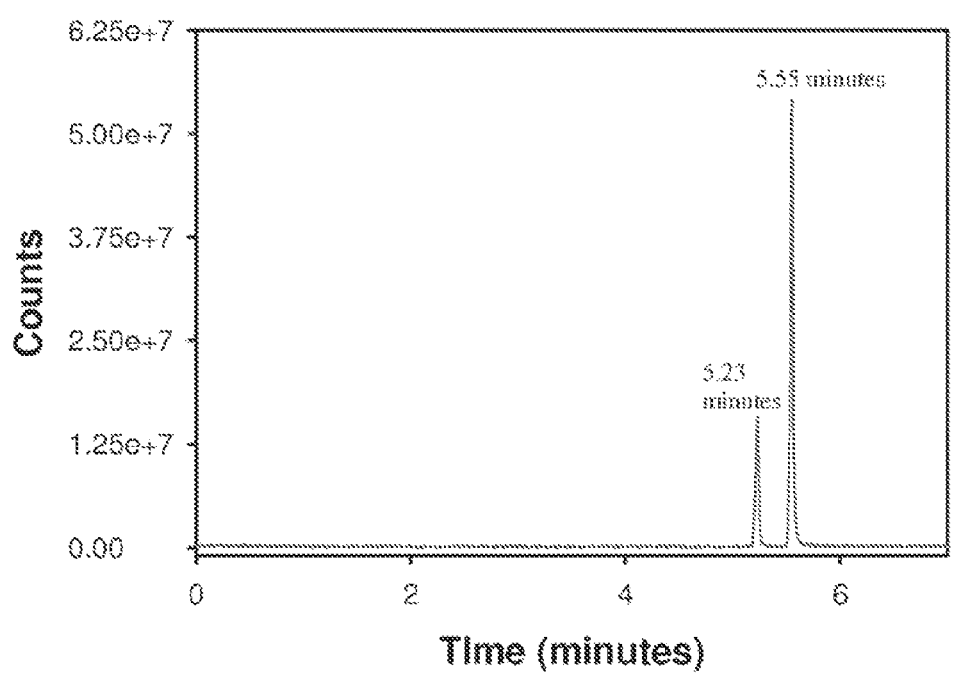
FIG. 18 is a LA-GC-MS chromatogram of 3,4-dinitrotoluene obtained using SIM.

Although not apparent in analyses of 1,2-dinitrobenzene using the LA-GC-NCD with both "Fast" and "Normal" methods, a small degradation peak at 5.53 minutes results from analysis of the compound with the LA-GC-MS interface when the normal method is used (FIG. 12). By using the NIST library search to match the spectrums produced by each peak, the first peak at 4.79 minutes was identified as the sample peak (1,2-dinitrobenzene) with 90.0% match probability and the second (5.53 minutes) was identified as 3,4-dinitrotoluene with 94.7% probability. In addition to 1,2-dintirobenzene and 2,4-dinitrotoluene, 3,4-dinitrotoluene also produces degradation products under the influence of the laser (FIG. 18). The first peak at 5.23 minutes and the second peak at 5.55 minutes was identified as 2,4-dinitrotoluene and 3,4-dinitrotoluene with respective NIST database match probabilities of 72.6% and 95.0%.

Figure 19:
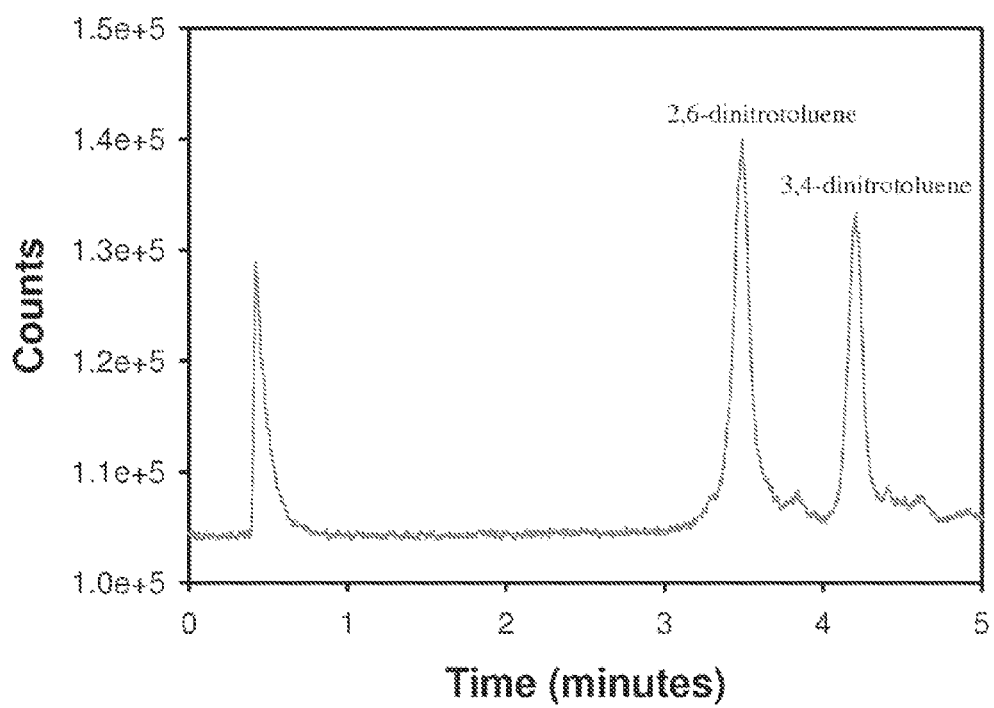
FIG. 19 is a LA-GC-NCD chromatogram showing separation of 2,6-DNT and 3,4-DNT.

In addition to conducting analysis around the 2 minute mark, mixtures of two explosives, 2,6-dinitrotoluene and 3,4 dinitrotoluene, can be resolved with the LA-GC-NCD using the method "Normal B" (FIG. 19).

All data used here for statistical analysis from repeats of experiments in May and June were gathered using 50 ppm concentrations of 2,6-dinitrotoluene whereas that collected in August was generated using 10 ppb concentrations of 2,6-dinitrotoluene. Differences among data at the 95% confidence interval are considered significant if p-values are less than 0.05.

Retention Time

Standard deviation and coefficient of variation (Table 5, 6 and 7) of LA-GC-NCD data used for all within day and next day comparisons based on peak area was high, indicating that the precision of results was very low. High precision was obtained however when retention time data was used as evidenced by the low standard deviation and coefficient of variation for this data (Table 5, 6 and 7). Similarly, within day repeatability comparisons using peak area data obtained with the LA-GC-NCD interface was low in all replicates for each day as indicated by the statistically significant differences established for nearly all comparisons (Table 8). However, when repeatability parameters where calculated using relative retention time, results dramatically improved as evidenced by no statistically significant differences for nearly every comparison (Table 8). In general next day repeatability comparisons (Table 9) followed the same trends as within day comparisons (all collections were in the same year).

TABLE 5

Standard deviation and coefficient of variation for peak area and relative retention time data from each replicate

| | June 2 Area | June 5 Area | June 2 RRT | June 5 RRT |
|---|---|---|---|---|
| | Standard Deviation | | | |
| Pad 1 | 3.55E+04 | 1.81E+04 | 7.62E−02 | 8.35E−02 |
| Pad 2 | 2.53E+04 | 7.35E+03 | 5.56E−02 | 6.97E−02 |
| Pad 3 | 4.90E+03 | 1.53E+04 | 5.88E−02 | 5.86E−02 |
| Pad 4 | 1.70E+04 | 9.37E+03 | 5.04E−02 | 1.36E−02 |
| | Coefficent of Variation | | | |
| Pad 1 | 3.81E+01 | 4.44E+01 | 2.50E+00 | 2.63E+00 |
| Pad 2 | 5.47E+01 | 5.19E+01 | 1.80E+00 | 2.22E+00 |
| Pad 3 | 9.78E+01 | 7.44E+01 | 1.92E+00 | 1.87E+00 |
| Pad 4 | 6.91E+01 | 3.82E+01 | 1.65E+00 | 4.25E−01 |

TABLE 6

Standard deviation and coefficient of variation for peak area and relative retention time data from each replicate

| | May 19 Area | May 23 Area | May 19 RRT | May 23 RRT |
|---|---|---|---|---|
| | Standard Deviation | | | |
| Pad 1 | 5.90E+04 | 1.58E+04 | 1.66E−01 | 4.35E−02 |
| Pad 2 | 3.21E+04 | 1.24E+04 | 2.16E−02 | 6.32E−02 |
| Pad 3 | 9.58E+03 | 2.90E+04 | 5.54E−02 | 1.59E−02 |
| Pad 4 | 2.60E+04 | 5.88E+03 | 1.75E−02 | 7.17E−02 |
| | Coefficient of Variation | | | |
| Pad 1 | 5.07E+01 | 3.14E+01 | 5.23E+00 | 1.39E+00 |
| Pad 2 | 8.98E+01 | 5.75E+01 | 6.89E−01 | 2.01E+00 |
| Pad 3 | 6.03E+01 | 8.84E+01 | 1.78E+00 | 4.96E−01 |
| Pad 4 | 9.11E+01 | 7.23E+01 | 5.56E−01 | 2.24E+00 |

TABLE 7

Standard deviation and coefficient of variation for peak area and relative retention time data from each replicate

| | August 8 Area | August 9 Area | August 8 RRT | August 9 RRT |
|---|---|---|---|---|
| | Standard Deviation | | | |
| Pad 1 | 5.44E+02 | 5.56E+02 | 8.90E−02 | 2.77E−02 |
| Pad 2 | 7.62E+01 | 1.64E+02 | 1.69E−02 | 2.88E−02 |
| | Coefficient of Variation | | | |
| Pad 1 | 4.54E+01 | 4.55E+01 | 2.50E+00 | 7.90E−01 |
| Pad 2 | 1.06E+01 | 1.52E+01 | 4.76E−01 | 8.17E−01 |

TABLE 8

T-test results for within day comparisons of 50 ppm 2,6-DNT peak area and relative retention time

| Date | Peak Area | Relative Retention Time |
|---|---|---|
| May 19 | | |
| Pad 1 vs. Pad 2 | 0.011 | 0.577 |
| Pad 1 vs. Pad 3 | 0.004 | 0.450 |
| Pad 1 vs. Pad 4 | 0.007 | 0.833 |
| Pad 2 vs. Pad 3 | 0.160 | 0.511 |
| Pad 2 vs. Pad 4 | 0.654 | 0.048 |
| Pad 3 vs. Pad 4 | 0.265 | 0.119 |
| May 23 | | |
| Pad 1 vs. Pad 2 | 0.006 | 0.895 |
| Pad 1 vs. Pad 3 | 0.24 | 0.017 |

TABLE 8-continued

T-test results for within day comparisons of 50 ppm 2,6-DNT peak area and relative retention time

| Date | Peak Area | Relative Retention Time |
|---|---|---|
| Pad 1 vs. Pad 4 | 0.001 | 0.092 |
| Pad 2 vs. Pad 3 | 0.415 | 0.059 |
| Pad 2 vs. Pad 4 | 0.032 | 0.146 |
| Pad 3 vs. Pad 4 | 0.096 | 0.967 |
| June 2 | | |
| Pad 1 vs. Pad 2 | 0.017 | 0.257 |
| Pad 1 vs. Pad 3 | 0.001 | 0.674 |
| Pad 1 vs. Pad 4 | 0.002 | 0.723 |
| Pad 2 vs. Pad 3 | 0.005 | 0.394 |
| Pad 2 vs. Pad 4 | 0.091 | 0.309 |
| Pad 3 vs. Pad 4 | 0.026 | 0.916 |
| June 5 | | |
| Pad 1 vs. Pad 2 | 0.009 | 0.461 |
| Pad 1 vs. Pad 3 | 0.045 | 0.289 |
| Pad 1 vs. Pad 4 | 0.067 | 0.627 |
| Pad 2 vs. Pad 3 | 0.345 | 0.740 |
| Pad 2 vs. Pad 4 | 0.056 | 0.126 |
| Pad 3 vs. Pad 4 | 0.585 | 0.040 |
| August 8 | | |
| Pad 1 vs. Pad 2 | 0.021 | 0.702 |
| August 9 | | |
| Pad 1 vs. Pad 2 | 0.468 | 0.252 |

TABLE 9

T-test results for next day comparisons of 50 ppm 2,6-DNT peak area and relative retention time

| Date | Peak Area | Relative Retention Time |
|---|---|---|
| 5/19 to 5/23 | 0.051 | 0.162 |
| 6/2 to 6/5 | 0.043 | 0.000 |
| 8/8 to 8/9 | 0.161 | 0.066 |

Washout and Defocusing

An experiment was conducted with the LA-GC-MS using 50 ppm 2,6-dinitrotoluene to determine the benefit of both washout steps and 1 mm defocusing of the laser beam to optimize both repeatability and desorption (Table 10). Following the same standard deviation and coefficient of variation trends for peak area and retention time in previous comparisons (Table 5-7), both standard deviation and coefficient of variation values were high for peak area and low for retention times for both normal and defocused analyses. No additional benefit could be established for 1 mm defocusing of the laser.

TABLE 10

Area and retention time for normal and defocused LA-GC-MS analysis with washout steps performed between each analysis.

| Normal | | Defocused 1 mm | |
|---|---|---|---|
| Area | Retention Time | Area | Retention Time |
| 2.11E+04 | 4.79E+00 | 4.97E+03 | 4.78E+00 |
| 2.40E+04 | 4.79E+00 | 2.96E+03 | 4.79E+00 |
| 3.25E+04 | 4.79E+00 | 6.85E+03 | 4.81E+00 |
| 1.89E+04 | 4.80E+00 | 3.89E+03 | 4.77E+00 |
| 1.85E+04 | 4.79E+00 | 2.14E+03 | 4.78E+00 |
| 3.71E+04 | 4.79E+00 | 1.69E+03 | 4.79E+00 |
| 1.64E+04 | 4.79E+00 | 8.94E+03 | 4.80E+00 |

TABLE 10-continued

Area and retention time for normal and defocused LA-GC-MS analysis with washout steps performed between each analysis.

| | Normal | | Defocused 1 mm | |
|---|---|---|---|---|
| | Area | Retention Time | Area | Retention Time |
| SD | 7.80E+03 | 3.78E−03 | 2.63E+03 | 1.35E−02 |
| CV | 3.24E+01 | 7.89E−02 | 5.87E+01 | 2.81E−01 |

Figure 20:
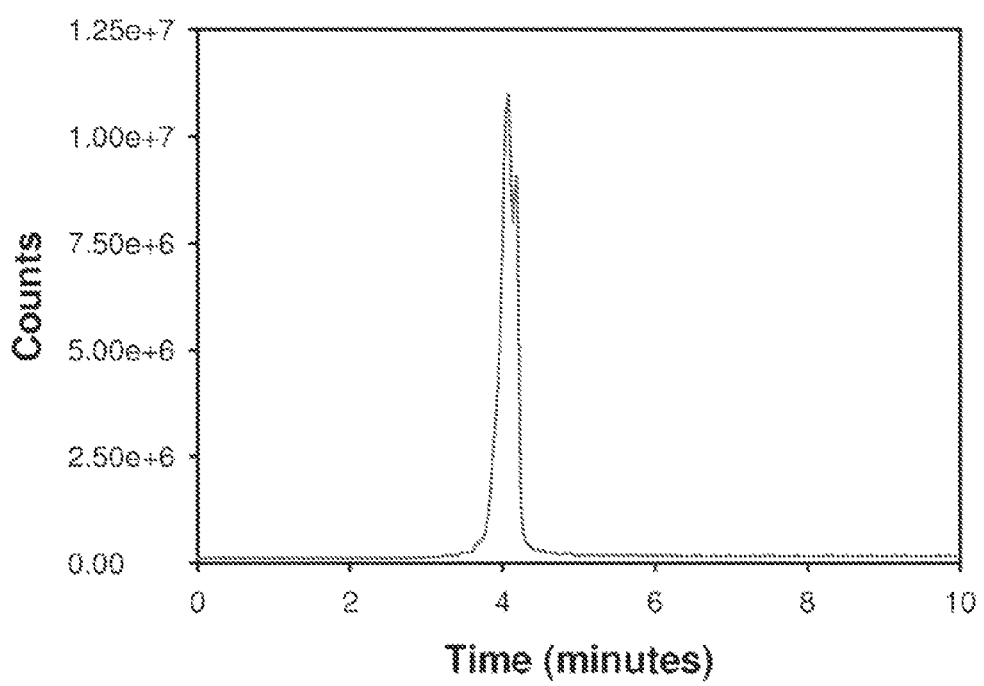
FIG. 20 is a LA-GC-NCD chromatogram of 50 ppm 2,6-dinitrotoluene.
Figure 21:
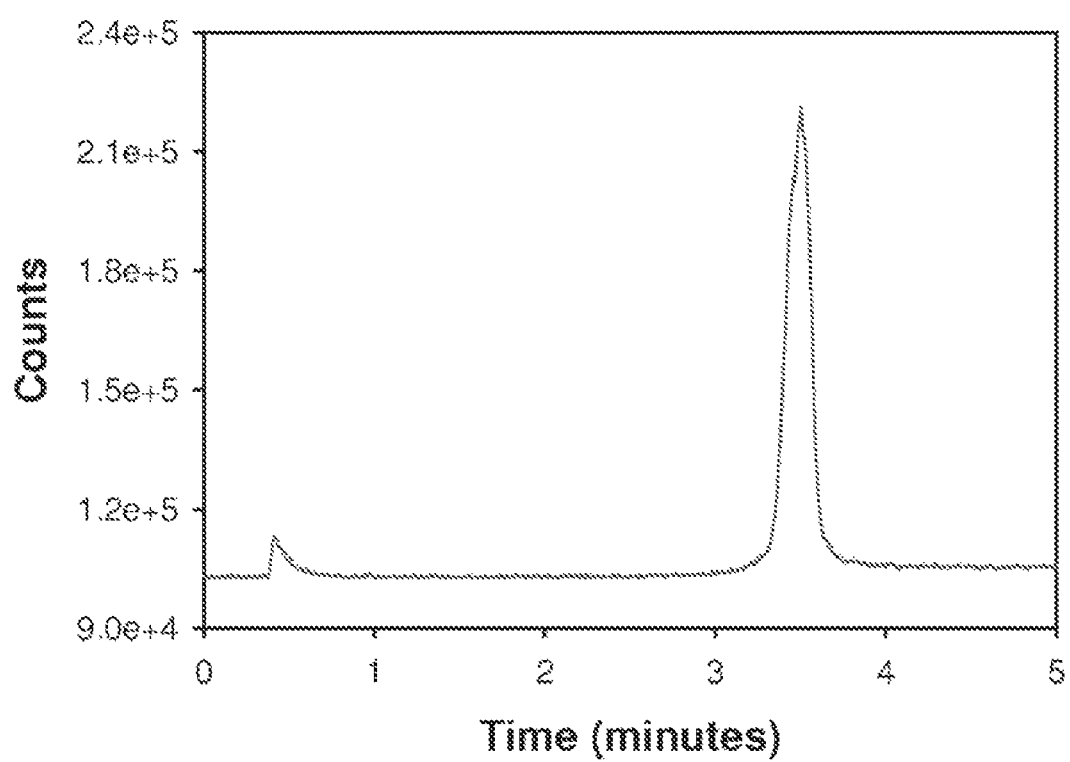
FIG. 21 is a LA-GC-NCD chromatogram of 50 ppm 2,6-dinitrotoluene obtained four months after the sampling represented in FIG. 20.

Two LA-GC-NCD analyses were conducted using identical samples of 50 ppm 2,6-dinitrotoluene. The first analysis was conducted in January when sample collection was first began (FIG. 20). The second was conducted in May (FIG. 21). The two chromatograms reveal a decrease in sensitivity of two orders of magnitude.

Figure 22:
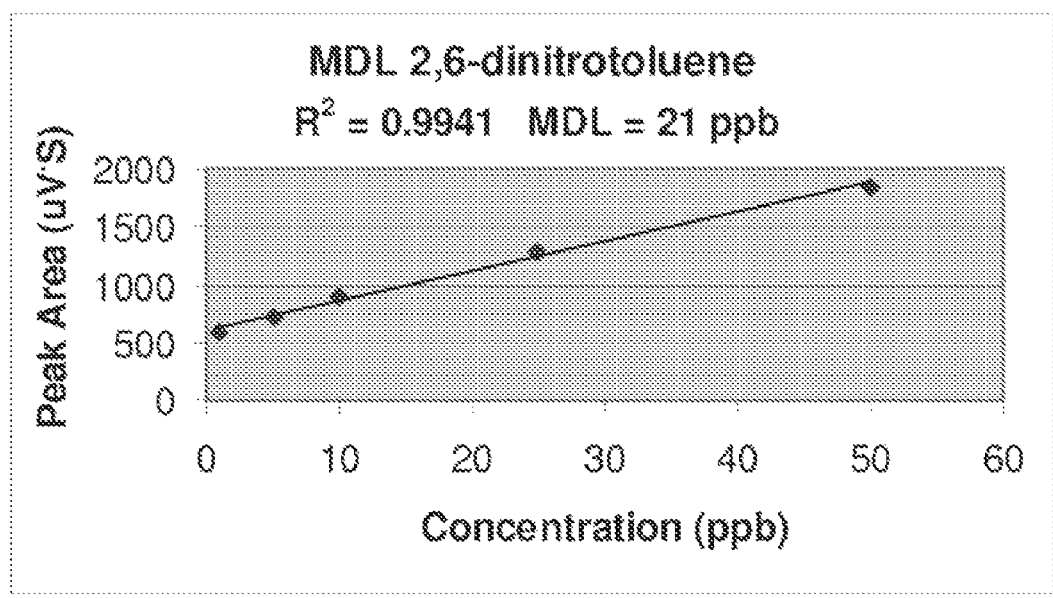
FIG. 22 shows a calibration curve and MDL for 2,6-dinitrotoluene.
Figure 23:
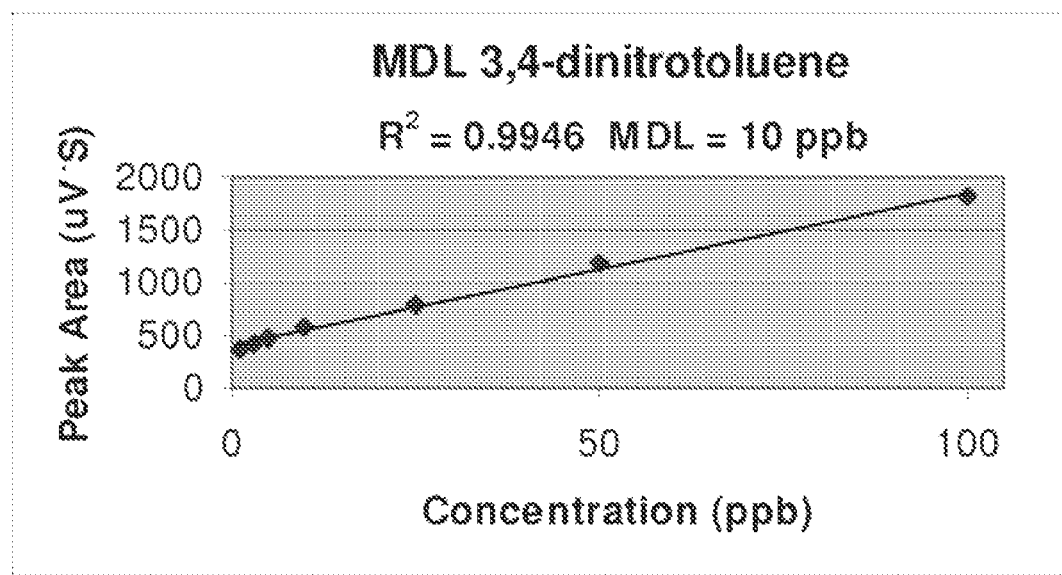
FIG. 23 shows a calibration curve and MDL for 3,4-dinitrotoluene.

Method detection limits (MDL's) were obtained for 2,6-dinitrotoluene and 3,4-dinitrotoluene using the LA-GC-NCD interface (FIGS. 22 and 23). While both compounds have the same vapor pressures, different MDL's were obtained. This could be due to changes in sensitivity and resolution of the NCD as the MDL for 2,6-dinitrotoluene was obtained two months previous to that of 3,4-dinitrotoluene. An additional cause, as evidenced by LA-GC-MS analysis (FIG. 18), is that 3,4-dinitrotoluene creates a degradation product fragment ion of 2,4-dinitrotoluene (5.23 minutes) and the amount of 3,4-dinitrotoluene lost as a degradation product during desorption may fluctuate in LA-GC-NCD analyses.

Discussion

Figure 9:
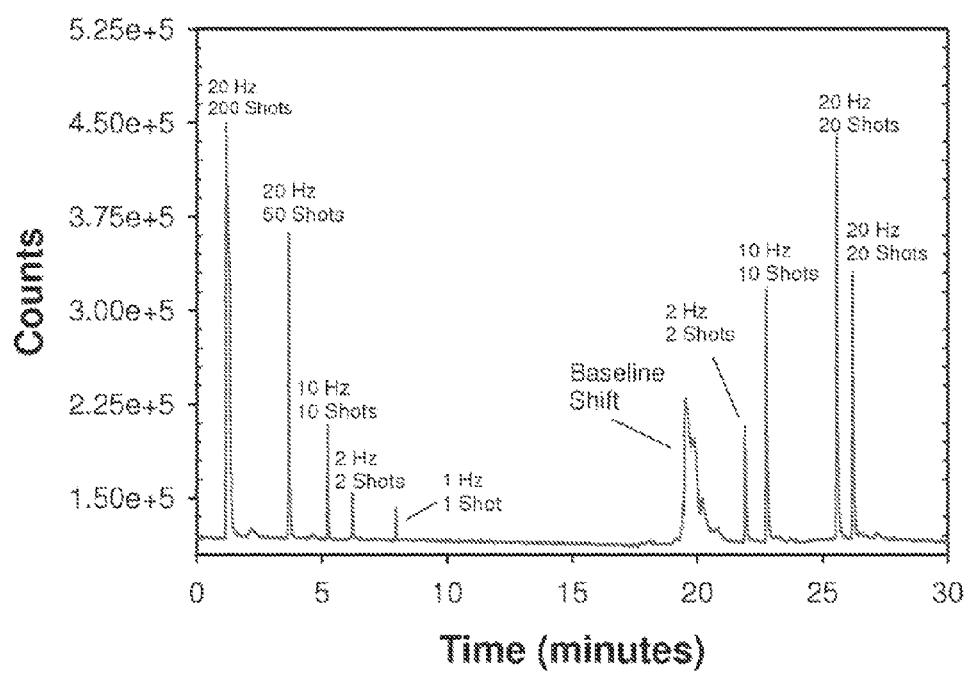
FIG. 9 shows a graph of signals from laser shots fired at blank filter pad (time 0-8 minutes) and filter loaded with Acetonitrile (19-27 minutes).

The laser peak (FIG. 7) could have various sources such as filter pad impurities or electromagnetic interference due to high pulse output power of the laser combined with insufficient shielding of the PMT in the NCD. On the other hand, the "laser peak" could also have some sample dependence as evidenced by higher signals that are obtained when the pad is loaded with acetonitrile (FIG. 9). The filter pad used for all analyses is composed only of polyvinyl alcohol, but it is possible that it contains some degree of nitrogen impurities that are detected by the nitrogen sensitive detector (FIGS. 7 and 9). The observed speed at which the "laser peak" is observed would indicate that if an impurity is present, it is (or becomes) a highly volatile, lightweight compound which is not impeded by the column stationary phase. Another alternative is that the beam is sending an electromagnetic pulse that is creating a response in the photomultiplier tube associated with the NCD. This phenomenon is not unheard of amongst scientist conducting various types of laser research when poor shielding of electrical components exists. When the LA-GC-MS interface is used, the laser peak is not observed (FIG. 8). This could be due to the better degree of shielding in the mass spectrometer or that the nitrogen signal detected by the MS, whose sensitivity is not specific for nitrogen, is detected as baseline noise. In either case, the signal intensity of the laser peak is more apparent when the magnitude of signal for the sample peak is lower (FIG. 19). When an abundance of sample is present however (FIG. 7) the laser peak is nearly non-existent indicating that the magnitude of the laser peak is a function of scale so long as the exact laser parameters are always used.

The LA-GC-NCD error associated with poor precision and peak area repeatability could be due to many reasons such as instability and energy changes in the beam at 50% energy, sample transfer from the sample cell through the unheated transfer line, particulate buildup in detector components such as reaction cell walls and burner assembly, and non uniformity of sample loaded onto the swipe matrix due to density changes across its area. Another likely culprit is column pre and post loading. Carrier gas is continually blowing over the filter pad in the chamber while the gas chromatograph is running or returning to initial analysis temperatures leading to increased evaporation of the explosive. Dry runs and solvent injections following analyses have been shown to assuage this problem, as evidenced by subsequent chromatograms with flat baselines, but they were not implemented until near the end of the data collection period. To alleviate unwanted column loading between analysis it is recommended that either a valve (4-way or more) equipped with a sample loop be used which can be vented between analyses as well as just after the laser has fired or that solvent cleanout steps be conducted using an appropriate solvent.

As can be seen with the variation of both normal and defocused peak area and retention time data as well as standard deviation and coefficient of variation of this data (Table 10), column washout steps with hexane did not alleviate the error associated with this technique. As evidenced by the smaller number of counts for defocused analysis, defocusing offers no additional benefit for desorption of the explosive from the sample swipe. In addition, coefficient of variation of defocused analysis is much higher indicating that less precision is obtained by defocusing the laser.

One of the most significant sources of poor LA-GC-NCD repeatability associated with this technique is the marked decrease observed in NCD sensitivity noticed over a four month period. In an attempt to alleviate this problem, the ceramic tubes within the NCD burner were replaced as well as the post and pre restrictor lines. Also, the walls of the ozone reaction cell were cleaned. None of these servicing steps led to increased sensitivity and resolution however. It was later discovered (after concluding data collection) that a microscopic hole had formed in the ozone generator assembly leading to decrease ozone production. This directly impacted the conversion of nitrate groups to the $NO_2$ radical which led to decreased sensitivity. In addition, the post restrictor line was partially obstructed which further decreased the amount of ozone available for reaction in the reaction chamber.

While standard deviation, coefficient of variation, within day repeatability, and next day repeatability statistical analyses were not favorable for peak area of chromatographic peaks obtained using the LA-GC-NCD interface, the technique shows promise for qualitative initial detection of TNT derivatives. In terms of retention times, the technique is much more reliable. It is believed the use of a flushing system or the valve, described supra, will avoid issues of cross-contamination between sampling. The LA-GC-MS interface is adequate for providing comparable results to data generated using the LA-GC-NCD and the on-board NIST database is useful for confirmation and identification of chromatographic peaks, indicating that the MS would be a good choice for orthogonal detection if the NCD and MS were combined in one interface. Future work in this area will add a heated transfer line as well as sub-zero cooling of the sample cell to prevent carry over in both the transfer line and in the sample cell and capillary column.

REFERENCES

Abrams, J. N., Rhodes, J. E., Smith, B. J., Smith, L. L. 2000. Multiservice Procedures for Nuclear, Biological, and Chemical (NBC) Defense of Theater Fixed Sites, Ports, and Airfields. Multiservice Tactics, Techniques, and Procedures.

Alexander, M. L.; Hemberger, P. H.; Cisper, M. E.; Nogar, N. S. 1993. Laser Desorption in a Quadrapole Ion Trap: Mixture Analysis Using Positive and Negative Ions. Analytical Chemistry. 65: 1609-1614.

Bell, C. A., Uhl, J. R., Hadfield, T. L., David, J. C., Meyer, R. F., and Smith, T. F. 2003. Detection of *Bacillus anthracis* DNA by LightCycler PCR. Journal of Clinical Microbiology. 40(8): 2897-2902.

Carter, J. C., Angel, S. M., Lawrence-Snyder, M., Scaffidi, J., Whipple, R. E., Reynolds, J. G. 2005. Standoff Detection of High Explosive Materials at 50 Meters in Ambient Light Conditions Using a Small Raman Instrument. Applied Spectroscopy. 59(6): 769-775.

CDC (2005); Acceptable Biological Specimens Needed for Laboratory Testing for Anthrax. Retrieved Mar. 20, 2005 from: www.bt.cdc.gov/agent/anthrax/lab-testing/anthrax-specimens.asp Elobeid, M.; Chai, Y.; Clarke, D.; Hannigan, R.; and Russ, J. 2005. Speciation Analysis with GC-ICP-MS: Organometal detection in tobacco smoke. In, G. Holland and D. Bandura (eds.), Plasma Source Mass Spectrometry: Current Trends and Future Developments. Royal Society of Chemistry, London UK. 80-88.

Grob, R. L. and Eugene F. Barry, eds. *Modern Practice of Gas Chromatography* $4^{th}$ ed. Hoboken, N.J.: John Wiley & Sons, 2004.

Harper, R. J. Almirall, J. R., Furton, K. G. 2005. Identification of Dominant Odor Chemicals Emanating from Explosives for Use in Developing Optimal Training Aid Combinations and Mimics for Canine Detection. 67(2): 313-327.

Halasz, A., Groom, C., Zhou, E., Paquet, L., Beaulieu, C., Deschamps, S., Corriveau, A., Thiboutot, S., Ampleman, G., Dubois, C., Hawari, J. 2002. Detection of Explosives and their Degradation Products in Soil Environments. Journal of Chromatography A. 963: 411-418.

Jackson, S. (2001). The application of Nd:YAG lasers in LA-ICP-MS. Laser Ablation-ICP-MS in the Earth Sciences. Principles and Applications. P. Sylvester (Ed.). Mineralogical Association of Canada. Volume 29.

Korb, A. R. 1996. "Portable Fourier transform infrared spectroradiometer for field measurements of radiance and emissivity," Applied Optics 35, 1679.

Lebedev, A. T. 2005. Mass Spectrometry in Identification of Ecotoxicants Including Chemical and Biological Warfare Agents. Toxicology and Applied Pharmacology. 207: S451-S458.

Lide, D. R. and Frederikse, H. P. R. (eds.). 1995. *CRC Handbook of Chemisty and Physics* 1995-1996. ($76^{th}$ ed.). New York: CRC Press, Inc.

Lopez-Moreno, C., Palanco, S., Laserna, J. J., DeLucia, F., Miziolek, A. W., Rose, J., Walters, R. A., Whitehouse, A. I. 2006. Test of a Stand-off Laser-Induced Breakdown Spectroscopy Sensor for the Detection of Explosive Residues on Solid Surfaces. Journal of Analytical Atomic Spectrometry. 21: 55-60.

LoPresti, V. Guarding the Air We Breathe. Retrieved Oct. 5, 2006 from: www.lanl.gov/quarterly/q_spring03/basis_text.shtml Morgan, J. S., Bryden, W. A., Miragliotta, J. A., Aamodt, L. C. 1999. Improved Detection of Explosive Residues by Laser Thermal Desorption. Johns Hopkins APL Technical Digest. 20(3): 1999.

NRC (2001)-1; National Research Council of the National Academies. *Science and Technology for Army Homeland Security: Report* 2. The National Academy Press. Washington, D.C. 2001.

NRC (2001)-2; National Research Council of the National Academies. *Science and Technology for Army Homeland Security: Report* 1. The National Academy Press. Washington, D.C. 2001.

NRC (2004)-1; Committee on the Review of Existing and Potential Standoff Explosives Detection Techniques, National Research Council 2004, *Existing and Potential Standoff Explosives Detection Techniques*, National Academies Press, Washington, D.C.

NRC (2004)-2; National Research Council of the National Academies. Naval Forces' Defense Capabilities Against Chemical and Biological Warfare Threats. The National Academy Press. Washington, D.C. 2004.

Nyarady, S. A.; Barkley, R. M.; Sievers, R. E. 1985. Redox Chemiluminescence Detector: Application to Gas Chromatography. Analytical Chemistry. 57: 2074-2079.

Olson, V. A., Laue, T., Laker, M. T., Babkin, I. V., Drosten, C., Shchelkunov, S. N., Niedrig, M., Damon, I. K., and Meyer, H.2004. Real-Time PCR System for Detection of Orthopoxviruses and Simultaneous Identification of Smallpox Virus. Journal of Clinical Microbiology. 42(5): 1940-1946.

Pinnaduwage, L. A.; Gehl, A.; Hedden, D. L.; Muralidharan, G.; Thundat, T.; Lareau, R. T.; Sulchek, T.; Manning, L.; Rogers, B.; Jones, M.; Adams, J. D. 2003 Explosives: A Microsensor for Trinitrotoluene Vapour. Nature. 425: 474.

USHC (2006); U.S. Homeland Security (2002). *National Strategy For Homeland Security*. Retrieved Oct. 27, 2006 from: (www.whitehouse.gov/homeland/book/nat_strat_hls.pdf).

Vorm, O., Roepstorff, P., and Mann, M. 1994. Improved Resolution and Very High Sensitivity in MALDI TOF of Matrix Surfaces Made by Fast Evaporation. Analytical Chemistry. 66: 3281-3287.

Weickhardt, C. and Tonnies, K. 2003. Rapid Analysis of Complex Mixtures by Means of Resonant Laser Ionization Mass Spectrometry. In, Laser in Environmental and Life Sciences. Hering, P., Lay, J. P., Stry, S. (eds.), Springer Verlag, New York. 193

Yan, X. 2002. Sulfur and Nitrogen Chemiluminescence Detection in Gas Chromatographic analysis. Journal of Chromatography A. 976: 3-10.

Yan, X. 1999. Detection by Ozone-Induced Chemiluminescence in Chromatography. Journal of Chromatography A. 842: 267-308.

Yinon, J. and Zitrin, S. 1993, *Modern Methods and Applications in Analysis of Explosives*, John Wiley & Sons Ltd, West Sussex, England.
-221.

Yinon, J. 2002. Field Detection and Monitoring of Explosives. Trends in Analytical Chemistry. 21(4): 292-301.

What is claimed is:

1. An device for detection of a component of interest in a sample, the device comprising an ultraviolet laser for desorption of said component of interest from said sample, wherein the energy of the laser is spread over an area such that energy density is above desorption threshold, but such that said sample is not ablated, a sample cell having a volume of about 0.1 $cm^3$ to about 8.0 $cm^3$, and a detector selected from the group consisting of a mass spectrometer and nitrogen chemiluminescence detector.

2. The device of claim 1, wherein the energy of the laser is reduced by about 20% to about 70%.

3. The laser device of claim 1, wherein the energy of the laser is reduced by about 50%.

4. The laser device of claim 1, wherein the energy of the laser is about 0.7 mJ to about 1.0 mJ.

5. The laser device of claim 1, wherein the laser energy fluence is about 2.0 to about 3.0 $J/cm^2$.

6. The device of claim 1, wherein said sample cell has a volume of about 1 $cm^3$ to about 5.0 $cm^3$.

7. The device of claim 1, wherein said sample cell has a volume of about 5 $cm^3$.

8. The device of claim 1, further comprising a transfer line from said sample cell to said detector, the device having no stationary phase.

9. The device of claim 8, wherein said transfer line is heated.

10. The device of claim 8, further comprising a venting device.

11. A method of rapid detection of a component of interest in a sample, the method comprising introducing said sample into a sample cell having a volume of about 0.1 $cm^3$ to about 8.0 $cm^3$, desorping the sample with an ultraviolet laser wherein the laser energy is spread over an area such that energy density is above desorption threshold, but such that the sample is not ablated, and transferring any of the compound of interest through a transfer line from the cell to a detector selected from the group consisting of a mass spectrometer and nitrogen chemiluminescence detector.

12. The method of claim 11, wherein the sample is a solid sample.

13. The method of claim 11, wherein the component of interest is a component of a compound selected from the group consisting of an explosive compound, a biological compound, a chemical compound, and organic compound.

14. The method of claim 11, wherein the laser energy fluence is about 2.0 to about 3.0 $J/cm^2$.

15. The method of claim 11, wherein the device is vented between analysis.

* * * * *